United States Patent
Matsunaga et al.

(10) Patent No.: US 10,406,413 B2
(45) Date of Patent: Sep. 10, 2019

(54) ANALYSIS APPARATUS, ANALYSIS METHOD, AND RECORDING MEDIUM

(71) Applicant: SONY CORPORATION, Tokyo (JP)

(72) Inventors: Hideyuki Matsunaga, Kanagawa (JP); Kosei Yamashita, Kanagawa (JP)

(73) Assignee: SONY CORPORATION, Tokyo (JP)

(*) Notice: Subject to any disclaimer, the term of this patent is extended or adjusted under 35 U.S.C. 154(b) by 159 days.

(21) Appl. No.: 15/039,097

(22) PCT Filed: Oct. 3, 2014

(86) PCT No.: PCT/JP2014/076554
§ 371 (c)(1),
(2) Date: May 25, 2016

(87) PCT Pub. No.: WO2015/083429
PCT Pub. Date: Jun. 11, 2015

(65) Prior Publication Data
US 2017/0157480 A1   Jun. 8, 2017

(30) Foreign Application Priority Data
Dec. 5, 2013 (JP) ................................ 2013-251714

(51) Int. Cl.
*A63B 60/46* (2015.01)
*A63B 24/00* (2006.01)
(Continued)

(52) U.S. Cl.
CPC ............. *A63B 60/46* (2015.10); *A61B 5/11* (2013.01); *A63B 24/0062* (2013.01);
(Continued)

(58) Field of Classification Search
None
See application file for complete search history.

(56) References Cited

U.S. PATENT DOCUMENTS 3,945,646 A * 3/1976 Hammond ......... A63B 24/0003
473/223
4,940,236 A * 7/1990 Allen ..................... A63B 53/00
473/223
(Continued)

FOREIGN PATENT DOCUMENTS

JP   59-194761 A   11/1984
JP   07-168952 A   7/1995
(Continued)

OTHER PUBLICATIONS

Brody, "Physics of the tennis racket"; American Journal of Physics 47, 482 (1979).*
(Continued)

*Primary Examiner* — John C Kuan
(74) *Attorney, Agent, or Firm* — Chip Law Group

(57) ABSTRACT

Provided is an analysis apparatus including an acquisition unit that acquires vibration data showing a vibration generated in a first object by having a second object come into contact with a first position on the first object, a first analysis processing unit that specifies the first position by comparing a vibration characteristic shown by the vibration data, and a vibration characteristic defined for each position where the second object may come into contact with the first object, and a second analysis processing unit that estimates a velocity after the contact of the second object based on a velocity of the first object and the first position.

11 Claims, 15 Drawing Sheets

(51) Int. Cl.
   *A63B 49/00* (2015.01)
   *G01P 3/12* (2006.01)
   *G06K 9/00* (2006.01)
   *A61B 5/11* (2006.01)
   *G01P 15/18* (2013.01)
   *A63B 60/00* (2015.01)
   *A63B 102/02* (2015.01)
   *A63B 102/04* (2015.01)
   *A63B 102/16* (2015.01)
   *A63B 102/18* (2015.01)
   *A63B 102/32* (2015.01)

(52) U.S. Cl.
   CPC .............. *A63B 49/00* (2013.01); *G01P 3/12* (2013.01); *G01P 15/18* (2013.01); *G06K 9/00342* (2013.01); *G06K 9/00496* (2013.01); *A63B 2060/002* (2015.10); *A63B 2102/02* (2015.10); *A63B 2102/04* (2015.10); *A63B 2102/16* (2015.10); *A63B 2102/18* (2015.10); *A63B 2102/32* (2015.10); *A63B 2220/30* (2013.01); *A63B 2220/40* (2013.01); *A63B 2220/50* (2013.01); *A63B 2220/803* (2013.01); *A63B 2220/833* (2013.01); *A63B 2220/89* (2013.01); *A63B 2225/50* (2013.01)

(56) References Cited

U.S. PATENT DOCUMENTS

| | | | | | |
|---|---|---|---|---|---|
| 6,134,965 | A | * | 10/2000 | Somville | A63B 49/00 73/570 |
| 2003/0008725 | A1 | * | 1/2003 | Erickson | G01N 29/045 473/282 |
| 2005/0239583 | A1 | * | 10/2005 | Damen | A63B 24/0021 473/516 |
| 2006/0084516 | A1 | * | 4/2006 | Eyestone | A63B 69/3632 473/219 |
| 2007/0105664 | A1 | * | 5/2007 | Scheinert | A63B 49/00 473/461 |
| 2009/0221388 | A1 | * | 9/2009 | Giannetti | A63B 69/0002 473/457 |
| 2010/0304877 | A1 | * | 12/2010 | Iwahashi | A63B 69/3632 473/223 |
| 2011/0151987 | A1 | * | 6/2011 | Golden | A63B 24/0003 473/223 |
| 2012/0116548 | A1 | * | 5/2012 | Goree | A61B 5/1118 700/90 |
| 2014/0180451 | A1 | * | 6/2014 | Marty | G09B 19/0038 700/91 |
| 2014/0290332 | A1 | * | 10/2014 | Yamashita | A63B 69/36 73/11.01 |
| 2015/0057112 | A1 | * | 2/2015 | Sak | A63B 24/0003 473/461 |
| 2015/0120021 | A1 | * | 4/2015 | Kerhuel | A63B 69/38 700/91 |

FOREIGN PATENT DOCUMENTS

| | | |
|---|---|---|
| JP | 2004-065570 A | 3/2004 |
| JP | 2011-050674 A | 3/2011 |
| WO | 2013/069447 A | 5/2013 |

OTHER PUBLICATIONS

Cross, "Impact of a ball with a bat or racket" American Journal of Physics 67, 692 (1999).*

* cited by examiner

ANALYSIS APPARATUS, ANALYSIS METHOD, AND RECORDING MEDIUM

CROSS REFERENCE TO RELATED APPLICATIONS

This application is a U.S. National Phase of International Patent Application No. PCT/JP2014/076554 filed on Oct. 3, 2014, which claims priority benefit of Japanese Patent Application No. JP 2013-251714 filed in the Japan Patent Office on Dec. 5, 2013. Each of the above-referenced applications is hereby incorporated herein by reference in its entirety.

TECHNICAL FIELD

The present disclosure relates to an analysis apparatus, an analysis method, and a recording medium.

BACKGROUND ART

Up until now, many technologies have been developed that assist the movements of a user, by using sensing or analysis. As such technology, for example, in sports where a ball is hit by using a hitting tool, such as tennis, badminton, table tennis, golf or baseball, the frequency at which a ball is hit by the hitting tool and the position at which the ball is hit are detected, and these are presented as information to a user. As an example of such technology, Patent Literature 1 discloses technology, for example, which arranges sensors on a hitting surface of a tennis racket and the surroundings of this, detects where the ball hits the hitting surface, and notifies the frequency and position of this to a user.

CITATION LIST

Patent Literature

Patent Literature 1: JP S59-194761A

SUMMARY OF INVENTION

Technical Problem

In the technology disclosed in Patent Literature 1, a large number of sensors are arranged corresponding to each of the positions on the hitting surface of the tennis racket. In this way, it is possible to detect not only the frequency at which the ball has hit the hitting surface, but also where on the hitting surface the ball has hit. However, such a large number of sensors will take time to be installed after a user has purchased a hitting tool. While hitting tools may be sold that have sensors built-in beforehand, the price of the hitting tool will increase, and it will be difficult for a user to replace the hitting tool. Further, while a method can also be considered where the instant the ball collides is photographed by using a high-speed camera capable of photographing with a frame rate of one several thousandth, and the position at which the ball is hit is confirmed from an image, a high-speed camera has a high cost, and the operation is also complex, and so it may be difficult for a user to easily use.

The same can be said for a swinging speed of a hitting tool, and a rotation axis, rotation amount, velocity or the like of a hitting ball. That is, while measuring these is useful for measuring the performance of a player, a high-cost exclusive apparatus, for example, a high-speed camera, a motion capture or the like, may be necessary for measurement. For example, while a method is known that analyzes an image photographed by a high-speed camera with a frame rate of approximately 4000 fps, and uses a Doppler radar, in order to obtain a rotation amount of a ball, an exclusive apparatus may become necessary, or advanced technology may be necessary for analysis and operation, and so it may be difficult for a user to easily use.

Accordingly, the present disclosure proposes a new and improved analysis apparatus, analysis method, and recording medium, capable of analyzing a contact phenomenon between objects with a simpler configuration.

Solution to Problem

According to the present disclosure, there is provided an analysis apparatus including: an acquisition unit configured to acquire vibration data showing a vibration generated in a first object by having a second object come into contact with a first position on the first object; a first analysis processing unit configured to specify the first position by comparing a vibration characteristic shown by the vibration data, and a vibration characteristic defined for each position where the second object may come into contact with the first object; and a second analysis processing unit configured to estimate a velocity after the contact of the second object based on a velocity of the first object and the first position.

According to the present disclosure, there is provided an analysis method including: acquiring vibration data showing a vibration generated in a first object by having a second object come into contact with a first position on the first object; specifying the first position by comparing a vibration characteristic shown by the vibration data, and a vibration characteristic defined for each position where the second object may come into contact with the first object; and estimating a velocity after the contact of the second object based on a velocity of the first object and the first position.

According to the present disclosure, there is provided a recording medium having a program stored therein, the program causing a computer to implement: a function of acquiring vibration data showing a vibration generated in a first object by having a second object come into contact with a first position on the first object; a function of specifying the first position by comparing a vibration characteristic shown by the vibration data, and a vibration characteristic defined for each position where the second object may come into contact with the first object; and a function of estimating a velocity after the contact of the second object based on a velocity of the first object and the first position.

Advantageous Effects of Invention

According to the present disclosure such as described above, a contact phenomenon between objects can be analyzed with a simpler configuration.

Note that, the above described effect is not necessarily limited, and any of the effects shown in the present disclosure, or other effects that can be understood from the present disclosure, may be accomplished along with the above described effect or instead of the above described effect.

DESCRIPTION OF EMBODIMENT(S)

Figure 1:
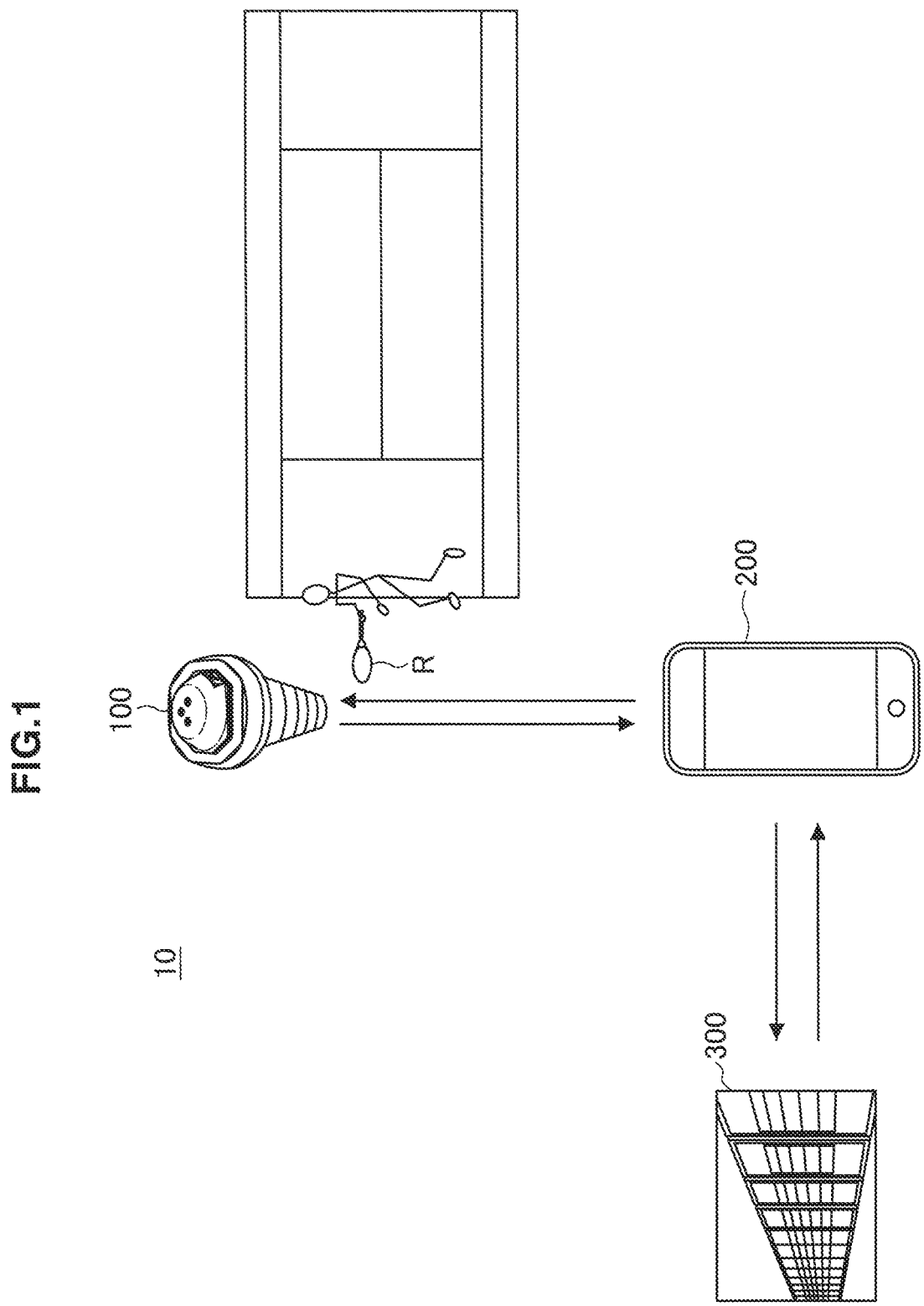
FIG. 1 is a figure that shows an example of a system configuration according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
1. System configuration
2. Function configuration
3. Process flow
4. Estimation of the velocity of the ball after a collision
   4-1. Calculation of an impulse
   4-2. Calculation of an effective mass of the racket
   4-3. Calculation of the velocity of the racket before a collision
   4-4. Selection of a restitution coefficient
5. Estimation of the rotation of the ball
6. Examples of information presentation
7. Hardware configurations
8. Conclusion
(1. System Configuration)

FIG. 1 is a figure that shows an example of a system configuration according to an embodiment of the present disclosure. With reference to FIG. 1, the system 10 includes a sensor apparatus 100, a smart phone 200, and a server 300.

The sensor apparatus 100 is mounted on a tennis racket R. The sensor apparatus 100 includes a vibration sensor, and detects vibrations generated in the racket R due to a ball colliding with the racket R. For example, vibration data acquired by the vibration sensor is transmitted to the smart phone 200 by wireless communication such as Bluetooth (registered trademark). Further, the sensor apparatus 100 may include an acceleration sensor, an angular velocity sensor, a magnetic field sensor or the like (for example, a nine axis motion sensor), and may detect an acceleration, angular velocity, inclination or the like of the racket R. The data acquired by these sensors is also transmitted to the smart phone 200 by wireless communication.

Here, the racket R is a hitting tool for hitting a ball in tennis. In an embodiment that will be described hereinafter, while a description will be made by setting, as an example, the racket R as a hitting tool, the example of a hitting tool is not limited to this. As will be described below, the present technology estimates the velocity of a ball after a collision based on vibrations at the time when the ball collides with a hitting tool. Therefore, it is possible for the present technology to be applied to every kinds of hitting tools, such as a hitting tool in which vibrations are generated by a collision of a ball, for example, a badminton racket, a table tennis racket, a golf club, or a baseball bat. Further, the present technology can be applied even if not for a sport, if it is the case where vibrations are generated by a collision of objects. Further, a collision may be a soft contact. Therefore, it can be said that the present technology estimates the velocity of a second object after a contact, based on vibrations generated in a first object by the contact of the second object to the first object.

The smart phone 200 receives data transmitted from the sensor apparatus 100. The smart phone 200 may execute an analysis process such as an estimation of the velocity after a collision of a ball such as described below, based on the received data. In this case, the smart phone 200 may output an analysis result to a user, and may upload the analysis data to the server 300. Alternatively, the smart phone 200 may forward the received data to the server 300. In this case, the smart phone 200 may receive a result of the analysis process executed by the server 300, and may output this result to the user. Note that, the smart phone 200 may be replaced by another apparatus that includes a communication function, an analysis function, and an output function, for example, a tablet terminal, various types of personal computers or the like.

The server 300 communicates with the smart phone 200 via a network, and receives an analysis result of the data acquired in the sensor apparatus 100 or the data of this. In the case where data is received from the smart phone 200, the server 300 executes an analysis process such as an estimation of the velocity after a collision of a ball such as described below. The server 300 retains an analysis result uploaded from the smart phone 200 or an analysis result calculated from the server 300 itself, and transmits this analysis result to a terminal apparatus used by the user such as the smart phone 200 as necessary. Further, the server 300 may transmit an analysis result to the terminal apparatus used by a user other than the user who has provided the analysis result or the data, and may enable sharing of the analysis result between the users.

(2. Function Configuration)

Figure 2:
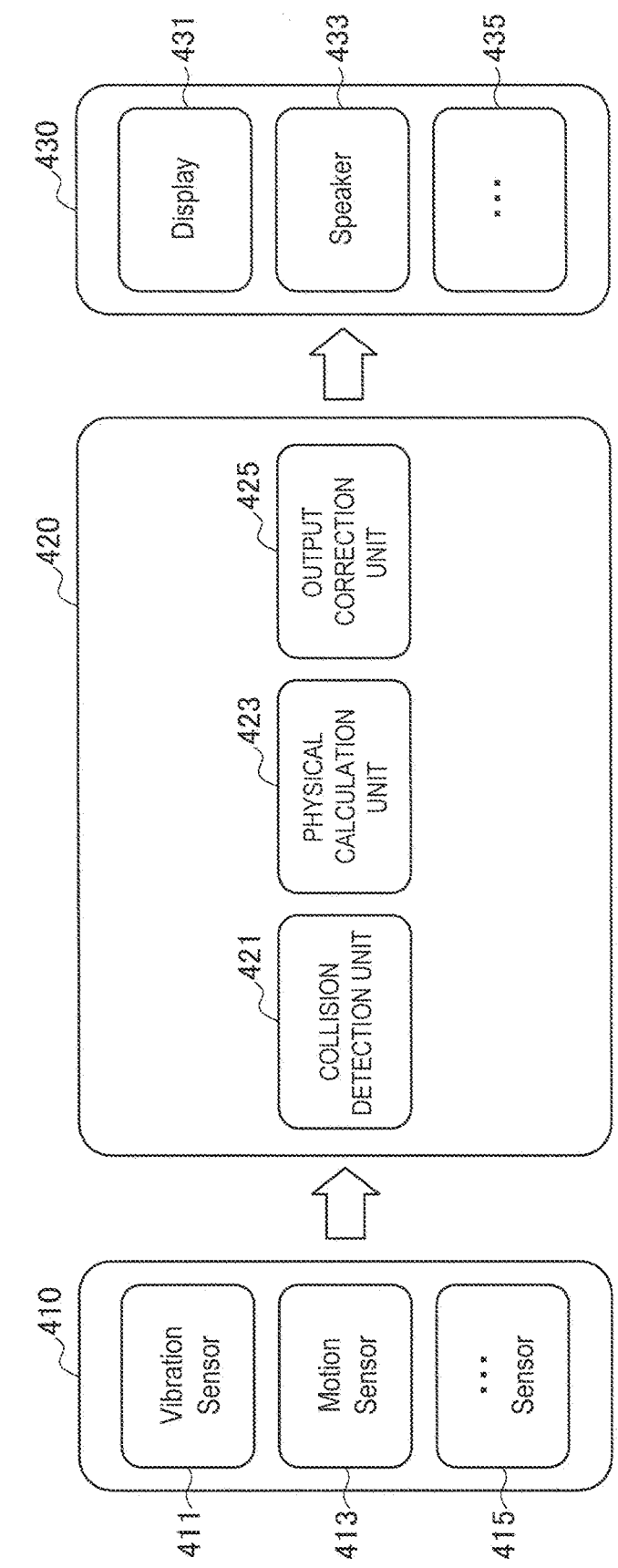
FIG. 2 is a figure that schematically shows a function configuration of a system according to an embodiment of the present disclosure.

FIG. 2 is a figure that schematically shows a function configuration of a system according to an embodiment of the present disclosure. With reference to FIG. 2, a system 40 includes, as a function configuration, an input unit 410, a processing unit 420, and an output unit 430. The function configuration of the system 40 may be implemented by distributing to a plurality of apparatuses. For example, in the system 10 described above with reference to FIG. 1, the input unit 410 may be implemented by the sensor apparatus 100, the processing unit 420 by the smart phone 200 or the server 300, and the output unit 430 by the smart phone 200. Alternatively, the function configuration of the system 40 may be implemented by consolidating in a single apparatus. For example, in the system 10 described above with reference to FIG. 1, the sensor apparatus 100 has a processor, a display, a speaker or the like, and may implement all of the input unit 410, the processing unit 420, and the output unit 430. Note that, in this case, the smart phone 200 and the server 300 may not be included in the system 10.

The input unit 410 may include, for example, a vibration sensor 411, a motion sensor 413, and another sensor 415. The vibration sensor 411 is implemented, for example, by a piezoelectric element, a strain gauge, an acceleration sensor or the like, and outputs vibration data for which vibrations generated in the racket R are detected. The motion sensor 413 is implemented, for example, by a three axis acceleration sensor, a three axis angular velocity sensor, a three axis geomagnetic sensor or the like (a sensor that includes all of these is also called a nine axis motion sensor), and outputs motion data for which an acceleration, rotation, direction or the like of (the portion where the sensor apparatus 100 has been attached of) the racket R is detected. Other than this, a temperature sensor, a pressure sensor, a GPS receiving device or the like may be included, as the another sensor 415. A detection result by the another sensor 415 may also be used in an analysis process such as an estimation of the velocity after a collision of a ball, which will be described below.

Here, in the case where the input unit 410 and the processing unit 420 are implemented in the same apparatus, the input unit 410 may be an acquisition unit that acquires vibration data showing vibrations generated in a first object (racket) by having a second object (ball) come into contact (collide) at a first position on the first object. The acquisition unit may additionally acquire motion data showing a displacement and rotation of the first object (racket) in a section including the contact (collision). Alternatively, in the case where the input unit 410 and the processing unit 420 are implemented in different apparatuses, vibration data or motion data acquired in the apparatus that implements the input unit 410 (for example, the sensor apparatus 100) is transmitted to the apparatus that implements the processing unit 420 (for example, the smart phone 200 or the server 300) by wired or wireless communication. In this case, it can be said that a communication apparatus receiving the vibration data or motion data in the apparatus that implements the processing unit 420 functions as the above acquisition unit.

The processing unit 420 may include, for example, a collision detection unit 421, a physical calculation unit 423, and an output correction unit 425. The collision detection unit 421 detects a collision of a ball to the racket R, based on the vibration data, and executes a process that accurately cuts out sensor data of the section where the collision is generated. For example, in the case of a sport, there are many cases where the contact time between a hitting tool and a ball is extremely short (in the case of tennis, 5 ms). Therefore, in order to estimate the state of a hitting tool before and after a collision, it is desirable for a sampling frequency of the motion sensor 413 to be 200 Hz or more. In this way, in order for the subsequent physical calculation unit 423 to execute an accurate analysis process with a realistic processing load, for the sensor data detected with a high sampling, it is desirable for the collision detection unit 421 to accurately cut out sensor data of the section where the collision is generated.

Figure 3:
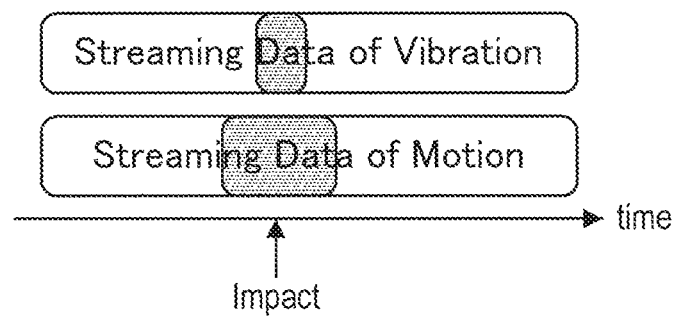
FIG. 3 is a figure for describing an example of the process of a collision detection unit according to an embodiment of the present disclosure.

FIG. 3 is a figure for describing an example of the process of a collision detection unit according to an embodiment of the present disclosure. With reference to FIG. 3, for example, in the case where an impact has been detected in the data of the vibration sensor 411, from among streaming data continuously provided from both the vibration sensor 411 and the motion sensor 413, the collision detection unit 421 cuts out streaming data of the vibration sensor of a section of a prescribed length following the impact, and streaming data of the motion sensor of a section of a prescribed length before and after the impact, as sensor data of the section where the collision is generated.

Figure 4:
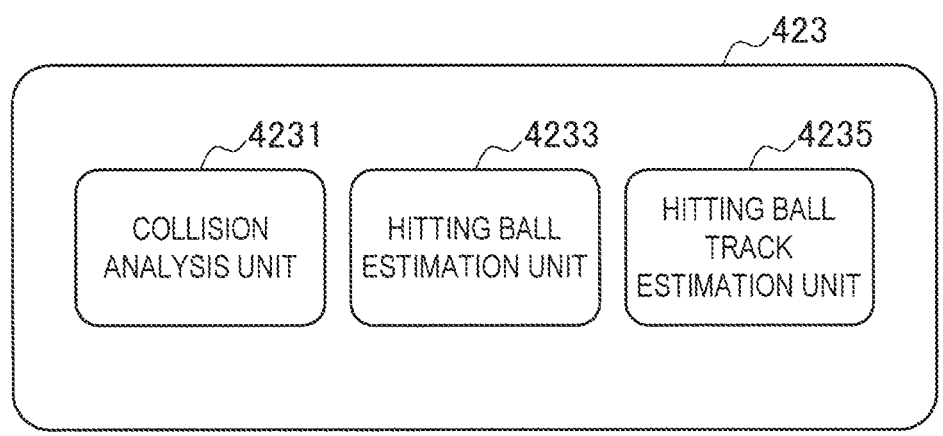
FIG. 4 is a figure for describing an example of the configuration of a physical calculation unit according to an embodiment of the present disclosure.

FIG. 4 is a figure for describing an example of the configuration of a physical calculation unit according to an embodiment of the present disclosure. With reference to FIG. 4, the physical calculation unit 423 included in the processing unit 420 includes a collision analysis unit 4231, a hitting ball estimation unit 4233, and a hitting ball track estimation unit 4235. The collision analysis unit 4231 estimates a velocity and posture of a hitting tool, and a track, at a collision section detected by the collision detection unit 421. Further, the collision analysis unit 4231 estimates a collision position of a ball on the hitting tool. The hitting ball estimation unit 4233 estimates the state of a hitting ball immediately after a collision. More specifically, for example, the hitting ball estimation unit 4233 estimates a velocity, rotation axis, rotation amount, and projecting direction of the hitting ball. The hitting ball track estimation unit 4235 estimates a track of the hitting ball. Further, the hitting ball track estimation unit 4235 may estimate a falling point of the hitting ball.

With reference again to FIG. 2, the output correction unit 425 included in the processing unit 420 corrects an output of the physical calculation unit 423. In the physical calculation unit 423, while a velocity or rotation of a ball is estimated by dynamically modelling and analyzing a collision between the racket R and the ball, in reality, there will be cases where the estimated value does not match with an actual value, due to a loss of kinetic energy by the racket or gut, a change of a restitution coefficient by the velocity of a ball before a collision, a change of a moment of inertia of the racket R by a swing or the like. Accordingly, the output correction unit 425 corrects an output of the physical calculation unit 423. Note that, in the case where a mismatch such as described above is not a problem, an output of the physical calculation unit 423 may be provided to the output unit 430 as it is, without including the output correction unit 425.

More specifically, for example, the output correction unit 425 may correct an output of the physical calculation unit 423 by using a statistical technique such as regression or machine learning. Further, for example, in addition to a value estimated by the physical calculation unit 423, the output correction unit 425 may correct an output of the physical calculation unit 423, by using other data capable of being used at a collision section, such as the movement of the racket R before and after a collision.

The output unit 430 may include, for example, a display 431, a speaker 433, and another output unit 435. The display 431 is, for example, various types of display devices such as an organic EL display, and outputs an output of the processing unit 420 towards a user as an image. The speaker 433 outputs an output of the processing unit 420 towards a user as a voice. The another output unit 435 can be, for example, a lamp such as an LED, a vibrator or the like, and outputs an output of the processing unit 420 towards a user as a light emission or vibrations. Note that, examples of information presentation by the display 431 will be described below, as examples of information output by the output unit 430.

(3. Process Flow)

Figure 5:
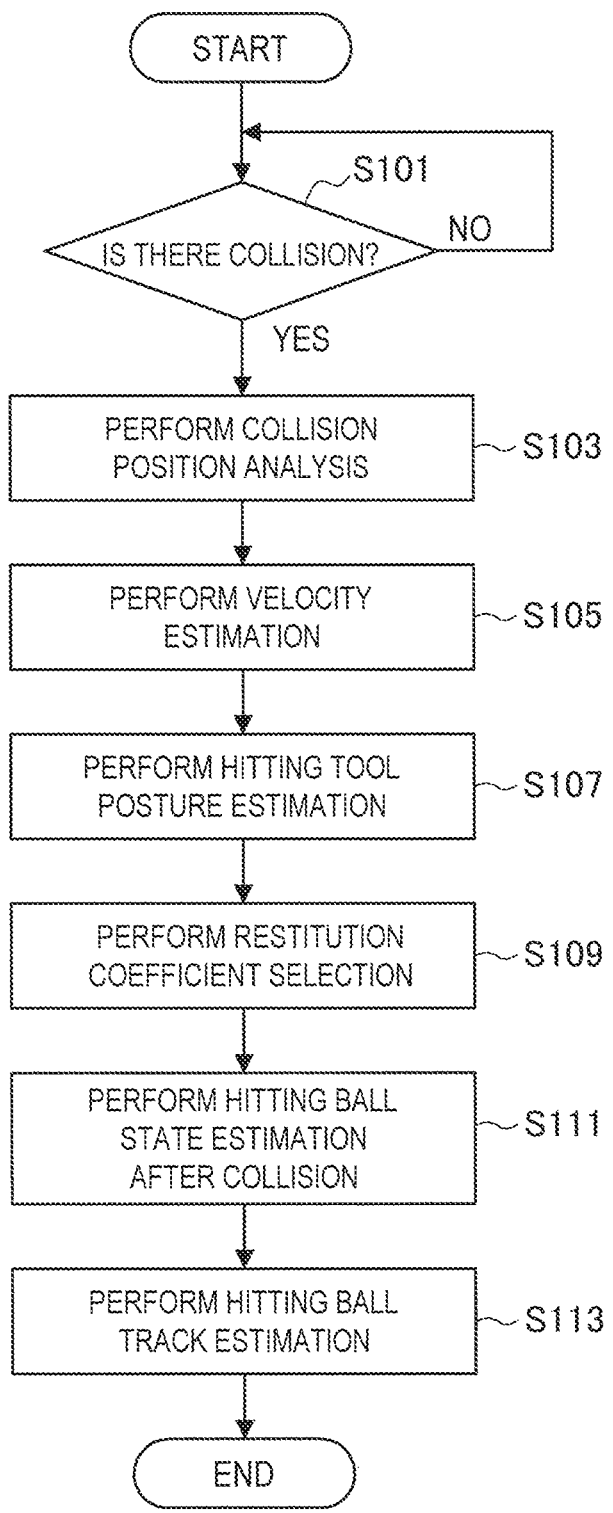
FIG. 5 is a flow chart that schematically shows the processes in an embodiment of the present disclosure.

FIG. 5 is a flow chart that schematically shows the processes in an embodiment of the present disclosure. The illustrated steps are executed in the processing unit 420. With reference to FIG. 5, first the collision detection unit 421 waits for the generation of a collision (S101). In the case where a collision is generated, the collision detection unit 421 provides sensor data of a collision section to the physical calculation unit 423, and a process is started by the physical calculation unit 423.

In the physical calculation unit 423, first the collision analysis unit 4231 analyzes a collision position (S103). More specifically, the collision analysis unit 4231 specifies a collision position of a ball on the racket R. This process may be a process, for example, that specifies a collision position where the ball collides of the racket R, by comparing a vibration characteristic of vibration data, and a vibration characteristic for each position where the ball collides of the racket R, based on vibration data for which vibrations of the time when the ball collides with the racket R are detected by the sensor apparatus 100 mounted at a portion different to the portion where the ball collides of the racket R. Note that, the details of such a process are described, for example, in WO 2013/069447.

Next, the hitting ball estimation unit 4233 executes an estimation related to the hitting ball after a collision. First, the hitting ball estimation unit 4233 estimates the velocity of the racket R at the collision position (S105). More specifically, first the hitting ball estimation unit 4233 estimates the velocity of the racket R at the time of a collision at an attachment position of the sensor apparatus 100 based on an acceleration change of the racket R, for example, detected by the motion sensor 413. In addition, the hitting ball estimation unit 4233 converts the velocity at the attachment position of the sensor apparatus 100 into a velocity of the racket R at the collision position, based on a rotation of the racket R, for example, detected by the motion sensor 413. At this time, the hitting ball estimation unit 4233 may calculate a posture of the racket R at the time of a collision and/or before and after this, based on an acceleration, rotation, and direction of the racket R, for example, detected by the motion sensor 413 (S107).

Next, the hitting ball estimation unit 4233 selects or calculates a restitution coefficient at the collision between the racket R and the ball (S109). Here, the restitution coefficient at the collision may be different in accordance with the collision position of the ball. The hitting ball estimation unit 4233 may calculate, for example, an effective mass of the racket R at the collision position, and may calculate an apparent restitution coefficient between the racket R and the ball at the collision position based on the effective mass. Alternatively, the hitting ball estimation unit 4233 may select one corresponding to the collision position estimated in S103, from among apparent restitution coefficients for each collision position measured beforehand.

In addition, the hitting ball estimation unit 4233 estimates a hitting ball state after a collision, based on a physical amount calculated or selected in the processes up until here (S111). For example, the hitting ball estimation unit 4233 estimates a velocity, hitting angle, rotation amount, rotation axis or the like of the ball after a collision. Here, the hitting ball estimation unit 4233 can restore an input waveform from detected vibration data, that is, a time change of power that the racket R receives from the ball, based on a vibration characteristic of the racket defined for the collision position estimated by the collision analysis unit 4231. In this way, an impulse given to the ball by the racket R can be calculated. Note that, an estimation of the velocity and rotation of the ball after a collision will be additionally described in detail below. To continue, the hitting ball track estimation unit 4235 may estimate a track of the hitting ball after a collision (S113).

In an embodiment of the present disclosure such as described above, it can be said that the collision analysis unit 4231 is a first analysis processing unit that specifies a first position (the collision position of the ball on the racket) by comparing a vibration characteristic shown by vibration data, and a vibration characteristic defined for each position where a second object (ball) may come into contact (collide) for a first object (racket). Further, it can be said that the hitting ball estimation unit 4233 is a second analysis processing unit that estimates a velocity after the contact (collision) of the second object (ball), based on a velocity of the first object (racket), and the first position (the collision position of the ball on the racket). Further, it can be said that the hitting ball track estimation unit 4235 is a third analysis processing unit that estimates a track after the contact of the second object (ball), based on the velocity after the contact (collision) of the second object.

Hereinafter, an estimation of the velocity and rotation of the ball after a collision executed by these processing units will be additionally described in detail.

(4. Estimation of the Velocity of the Ball after a Collision)

Figure 6:
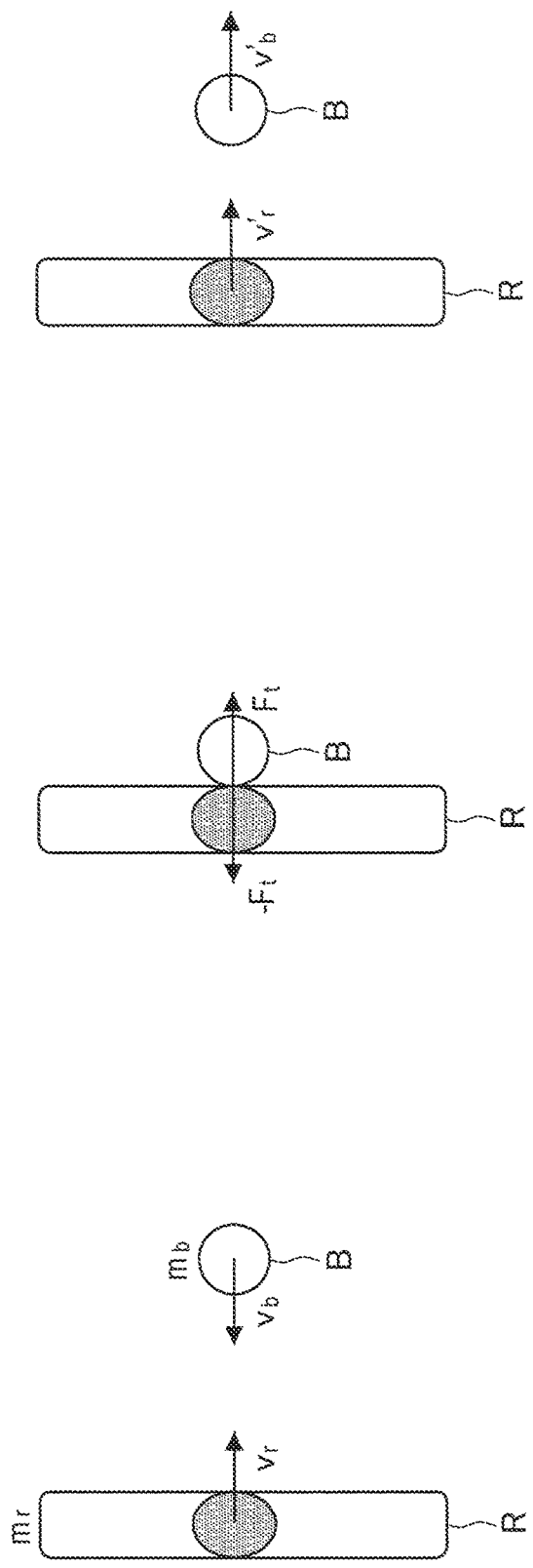
FIG. 6 is a figure that schematically shows a collision phenomenon analyzed in an embodiment of the present disclosure.

FIG. 6 is a figure that schematically shows a collision phenomenon analyzed in an embodiment of the present disclosure. With reference to FIG. 6, the racket R and the ball B are shown. The mass of the racket R is $m_r$, the mass of the ball B is $m_b$, and these do not change through before a collision shown in (a), during a collision shown in (b), and after a collision shown in (c).

In the stage before a collision shown in (a), the racket R moves towards the ball B with a velocity $v_r$, and the ball B moves towards the racket R with a velocity $v_b$. In the stage during a collision shown in (b), the racket R receives an impulse of $-F_t$ from the ball B, and the ball B receives an impulse of $F_t$ from the racket R. In addition, in the stage after a collision shown in (c), the velocity of the racket R changes to $v'_r$, and the velocity of the ball B changes to $v'_b$.

In relation to a collision phenomenon such as described above, the following Formula 1 to Formula 3 are established in accordance with the laws of mechanics. Note that, e is a restitution coefficient between the racket R and the ball B. Formula 1 is derived from a definition formula of a restitution coefficient, Formula 2 from the law of the conservation of momentum, and Formula 3 from a relationship between a change of momentum and an impulse.

[Math. 1]

$$e = -\frac{v'_b - v'_r}{v_b - v_r} \quad \text{(Formula 1)}$$

$$m_b v_b - m_b v'_b = m_r v'_r - m_r v_r + \quad \text{(Formula 2)}$$

$$-F_t = m_r v'_r - m_r v_r \quad \text{(Formula 3)}$$

The mass $m_r$ of the racket R and the mass $m_b$ of the ball B, from among the physical amounts related to the above collision phenomenon, can be measured beforehand. Note that, an effective mass at the position where the ball B collides with the racket R may be used, for the mass $m_r$ of the racket R. Further, in the present embodiment, the position where the ball B collides with the racket R (first position) can be specified, based on vibration data provided from the sensor apparatus 100 mounted on the racket R, and a particular transfer function of the racket R measured beforehand. It is possible for the sensor apparatus to additionally detect a displacement and rotation of the racket R at the mounting position of the sensor apparatus (second position). Therefore, if the shape of the racket R is already known on the basis of the mounting position of the sensor apparatus, motion can be reproduced in a three-dimensional space of the entire racket R, and the velocity of the racket R can be estimated at the first position at the point in time when the ball B collides with the racket R.

In addition, in the present embodiment, an input signal of vibrations at the first position, that is, a waveform of power exerted on the racket R by the ball B, can be reproduced, based on vibration data provided from the sensor apparatus mounted on the racket R, and a particular transfer function of the racket R measured beforehand. Since the impulse $F_t$ that the racket R receives from the ball B corresponds to a time integration of this waveform of power, in the present embodiment, it is also possible to perform a calculation in relation to the impulse $F_t$, based on the vibration data and the particular transfer function of the racket R. Further, as will be described below, it is also possible for a restitution coefficient e to be determined based on the position where the ball B collides with the racket R.

Then, the unknown quantities included in the above Formula 1 to Formula 3 are the three of the velocity $v'_r$ after a collision of the racket R, the velocity $v_b$ before a collision of the ball B, and a velocity $v'_b$ after a collision of the ball B. Therefore, the above Formula 1 through to Formula 3 can be solved as simultaneous equations for determining these three unknown quantities. As a result, the velocity $v'_b$ after a collision of the ball B can be obtained by the following Formula 4.

[Math. 2]

$$v'_b = \frac{v_r - \frac{F_t}{m_r} - e\left(\frac{F_t}{m_b} - v_r\right)}{1+e} \quad \text{(Formula 4)}$$

Note that, if the velocity $v'_r$ after a collision of the racket R can be measured, the velocities $V_b$ and $v'_b$ before and after a collision of the ball B can be obtained, for example, by solving Formula 1 and Formula 2 as simultaneous equations. However, since a high sampling frequency (200 Hz or more) may be necessary as the time when a collision is generated is extremely short (approximately 5 ms), and a detection value of a sensor changes significantly for a collision, in reality, it will be difficult to calculate the velocity $v'_r$ after a collision of the racket R, for example, from a detection value of an acceleration sensor.

Accordingly, in the present embodiment, the velocity $v'_b$ after a collision of the ball B is estimated, with the velocity $v'_r$ after a collision of the racket R unknown as it is, by using the possibility of a calculation of the impulse $F_t$ such as described above. Note that, as will be described below, in Formula 4, the accuracy of an estimation can be improved, by using an effective mass in place of the mass $m_r$ of the racket R, calculating the velocity $v_r$ of the racket before a collision for a collision position, and using an apparent restitution coefficient $e_A$ at the collision position as a restitution coefficient e.

(4-1. Calculation of an Impulse)

Figure 7:
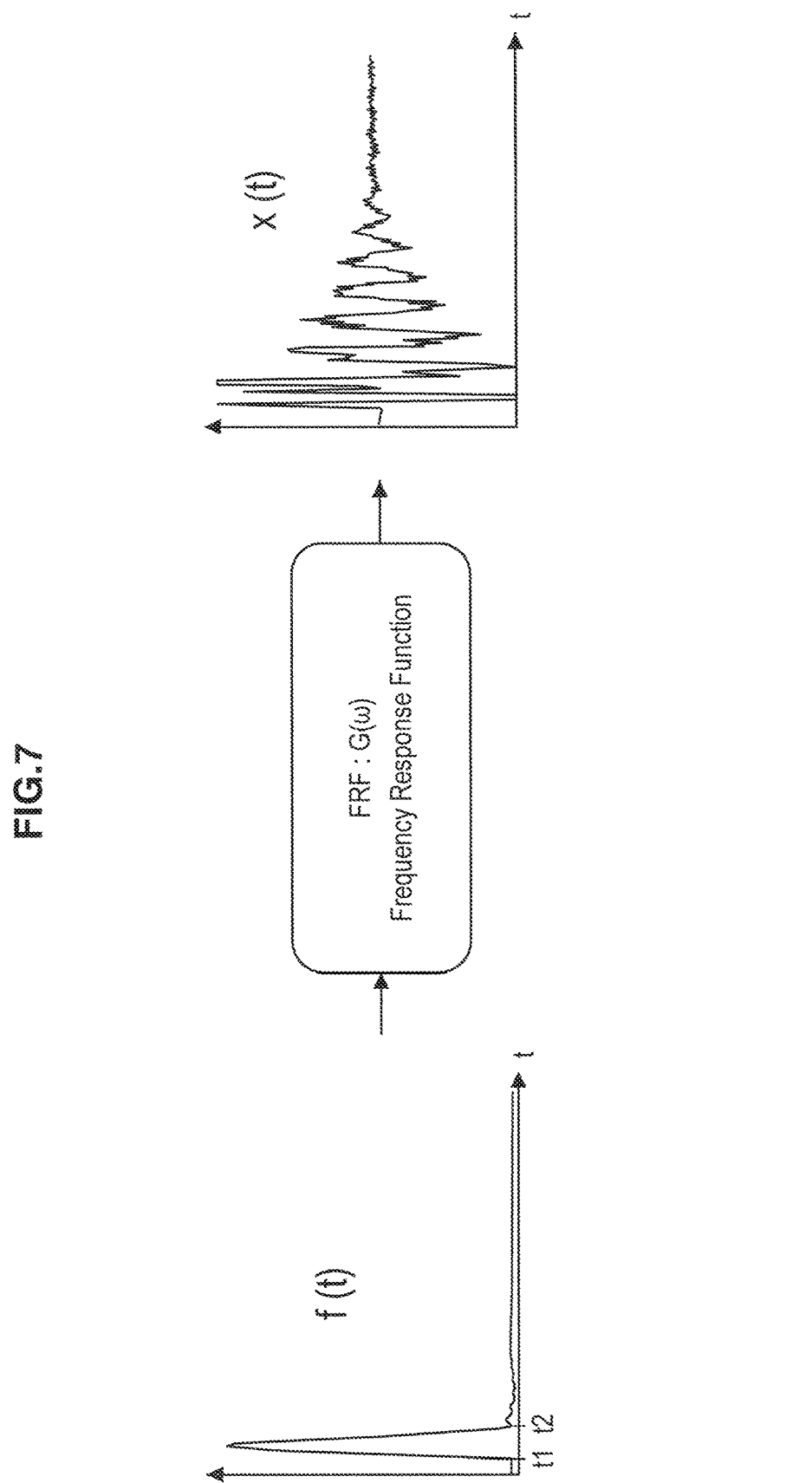
FIG. 7 is a figure for describing a calculation of an impulse in an embodiment of the present disclosure.

FIG. 7 is a figure for describing a calculation of an impulse in a first embodiment of the present disclosure. With reference to FIG. 7, a time waveform f(t) of an input signal at the position where the ball B collides with the racket R (first position) is transferred with a transfer function (FRF: Frequency Response Function) $G(j\omega)$, and is measured as a time waveform x(t) of an output signal at the mounting position of the sensor apparatus (second position). Here, when a frequency spectrum of the input signal is set to $F(j\omega)$, and a frequency spectrum of the output signal is set to $X(j\omega)$, the transfer function $G(j\omega)$ is represented as $G(j\omega)=X(j\omega)/F(j\omega)$.

Here, when a transfer function of the racket R at the first position is set to $G_{ip}(\omega)$, and a frequency spectrum of the input signal at the same first position is set to $F_{ip}(\omega)$ (ip is an abbreviation of an impact point), the relationship of $F_{ip}(\omega)=X(\omega)/G_{ip}(\omega)$ is established. Since $G_{ip}(\omega)$ may already known by a measurement beforehand, $F_{ip}(\omega)$ can be calculated, if $X(\omega)$ is specified based on vibration data provided from the sensor apparatus, based on the above relationship. In addition, the time waveform $f_{ip}(t)$ of the input signal at the first position can be obtained by $f_{ip}(t)=ifft(F_{ip}(\omega))$ (ifft is an abbreviation of an inverse fast fourier transform).

In addition, since the time waveform $f_{ip}(t)$ of the input signal represents a time change of the power transmitted from the ball B to the racket R, an impulse the ball B exerts on the racket R can be calculated by integrating this. When a collision start time is set to t1, and a collision end time is set to t2, in the time waveform $f_{ip}(t)$, the impulse $F_t$ can be obtained by the following Formula 5.

[Math. 3]

$$F_t = \int_{t_1}^{t_2} f_{ip}(t)dt \quad \text{(Formula 5)}$$

In this way, in the present embodiment, the impulse $F_t$ can be calculated from vibration data, by an inverse operation using a transfer function included in a vibration characteristic defined for the first position.

(4-2 Calculation of an Effective Mass of the Racket)

Next, a calculation of an effective mass of the racket will be described. In the above Formula 4, while the mass of the racket R is expressed as $m_r$, this mass $m_r$ may be expressed by an effective mass, in the case where the velocity of the ball B after a collision is to be more accurately calculated.

In the case where the ball B collides with the racket R, the racket R is pushed back and rotated, in accordance with the power transmitted from the ball B to the racket R. As a result, in the above Formula 1 to Formula 3 expressing a collision phenomenon, the mass of the racket R may be different to the actual mass of the racket R (for example, measured in a static state). More specifically, the mass of the racket R in Formula 1 to Formula 3 may be an effective mass $m_{re}$ smaller than the actual mass $m_r$.

Here, it is known that the effective mass $m_{re}$ of the racket R is calculated from the actual mass $m_r$, by the following Formula 6. Note that, by setting the x-axis to a width direction axis of the racket R, and the y-axis to a length direction axis of the racket R, y is a y-axis direction distance from the center of gravity of the racket R up to a collision position (first position) of the ball B, x is an x-axis direction distance from the center of gravity of the racket R up to the first position, $I_x$ is a moment of inertia around the x-axis of the racket R, and $I_y$ is a moment of inertia around the y-axis of the racket R.

[Math. 4]

$$\frac{1}{m_{re}} = \frac{1}{m_r} + \frac{y^2}{I_x} + \frac{x^2}{I_y} \quad \text{(Formula 6)}$$

In the present embodiment, it is possible for x and y, which are the distances of the x-axis and the y-axis from the center of gravity of the racket R up to a collision position (first position), to be calculated by having the first position specified. Further, the moments of inertia $I_x$ and $I_y$ may be measured for each defined collision position, and may be approximated by the following Formula 7 and Formula 8. Note that, L is the length of the racket R, and W is the width of the racket R.

[Math. 5]

$$I_x = \frac{m_r L^2}{12} \quad \text{(Formula 7)}$$

$$I_y = \frac{m_r W^2}{12} \quad \text{(Formula 8)}$$

In the case where the moments of inertia $I_x$ and $I_y$ are obtained by approximations, the effective mass $m_{re}$ of the racket R can be obtained by the following Formula 9 obtained by substituting Formula 7 and Formula 8 for the above Formula 6.

[Math. 6]

$$m_{re} = \frac{m_r}{1 + \frac{12y^2}{L^2} + \frac{12x^2}{W^2}} \quad \text{(Formula 9)}$$

(4-3 Calculation of the Velocity of the Racket Before a Collision)

Figure 8:
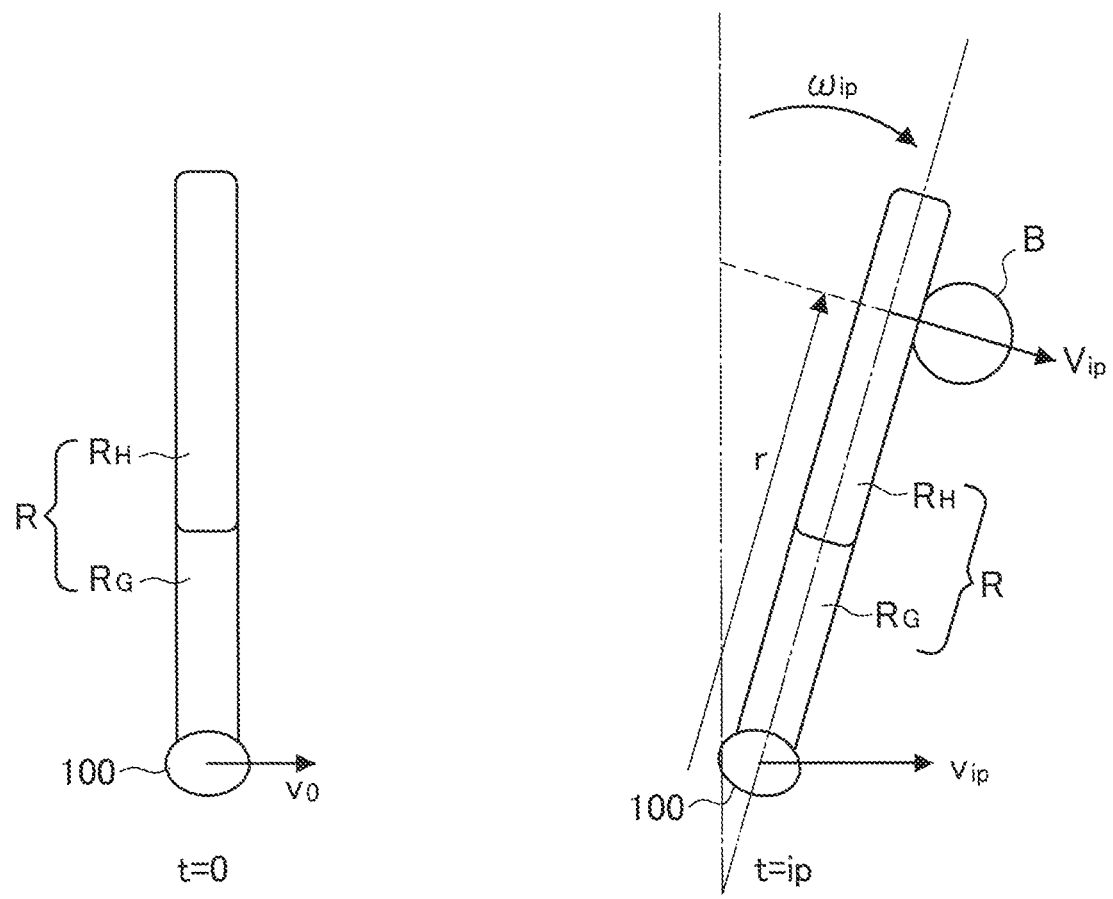
FIG. 8 is a figure for describing a calculation of the velocity of a racket before a collision in an embodiment of the present disclosure.

FIG. 8 is a figure for describing a calculation of the velocity of the racket before a collision in an embodiment of the present disclosure. In this example, the velocity before a collision of the racket R is calculated, based on the posture of the racket R estimated based on motion data. The calculated velocity can be used for an estimation of the velocity after a collision of the ball B. With reference to FIG. 8, the racket R and the ball B are shown. The racket R includes a club $R_G$ and a head $R_H$, and the sensor apparatus 100 is attached to the edge of the club $R_G$ (the grip end). In the initial state (t=0) shown in (a), the velocity of the sensor apparatus 100 is $v_0$, and the acceleration is $a_0$.

In the state at the time of a collision (t=$t_{ip}$) shown in (b), the velocity of the sensor apparatus 100 is $v_{ip}$, and the acceleration is $a_{ip}$. Further, the angular velocity of the sensor apparatus 100 is $\omega_{ip}$. In this state, the velocity V of the racket R at the collision position (first position) of the ball B in the head $R_H$ is obtained. First, since the velocity $v_{ip}$ of the sensor apparatus 100 is the result of the acceleration a(t) generated from the initial state (t=0) up until the time of a collision (t=$t_{ip}$), it can be obtained by the following Formula 10. Note that, $a(t)=a_0$, and $a(t_{ip})=a_{ip}$.

[Math. 7]

$$v_{ip} = v_0 + \int_0^{t_{ip}} a(t) dt \quad \text{(Formula 10)}$$

In addition, the velocity $v_{ip}$ generated at the collision position by the rotation of the racket, in the state at the time of a collision, can be obtained by the following Formula 11 by using a distance r from the grip end of the collision position.

[Math. 8]

$$V_{ip} = r\omega_{ip} \quad \text{(Formula 11)}$$

By the above description, the velocity $v_{rip}$ of the racket at the collision position, in the state at the time of a collision, can be obtained by the following Formula 12.

[Math. 9]

$$v_{rip} = v_{ip} + V_{ip} = v_0 + \int_0^{t_{ip}} a(t) dt + r\omega_{ip} \quad \text{(Formula 12)}$$

When the calculation of the velocity of the racket before a collision such as described above is generalized, it becomes as follows. First, data of a motion sensor (an acceleration sensor, angular velocity sensor or the like) included in the sensor apparatus 100 is analyzed, a posture calculation of the racket R at the section where a collision with the ball B is generated is executed, and a displacement and track are obtained. At this point of time, a displacement and track at the attachment position of the sensor apparatus 100 are calculated. Here, for example, information that includes a displacement and Euler angle in a three-dimensional space may be calculated, such as P={x, y, z, roll, pitch, yaw}.

In addition, the displacement and track at the attachment position of the sensor apparatus 100 obtained such as described above are converted into a displacement at the collision position (first position) with the ball B. At this time, for example, a displacement $P_{ip}$ at the collision position can be calculated, by detecting a rotation of the racket R by the angular velocity sensor included in the sensor apparatus 100, obtaining a rotation matrix $Rot_{ip}$, and converting a displacement P at the attachment position of the sensor apparatus 100. More specifically, for example, $P_{ip}$ can be obtained as $P_{ip}$=Rot*P.

In this way, the velocity (vector) at the collision position at the time of a collision can be obtained. The velocity after a collision of the ball B may be estimated, based on the direction of this vector (the velocity direction at the time of a collision of the racket R estimated based on the posture). Further, as will be described below, a rotation amount of the ball B may be estimated, based on the velocity direction at the time of a collision of the racket R. The angle of a collision surface (head $R_H$) of the racket R at the time of a collision can be obtained, based on the above P. A hitting angle of the ball B after a collision can be estimated, based on this angle, and the velocity direction of the racket R at the time of a collision.

Note that, for example, in the case where it is possible for the racket R to be regarded as static ($v_r$=0 or $v_{rip}$=0) before a collision, such as a volley shot in tennis, a calculation of the velocity of the racket R such as described above may not be necessary. Here, while motion data that includes an acceleration provided from the sensor apparatus 100 may be necessary for calculating the velocity $v_r$ or $v_{rip}$, motion data may not be necessary for a calculation of the impulse $F_r$, mass $m_r$ (or effective mass $m_{re}$), mass $m_b$, and restitution coefficient e (or apparent restitution coefficient $e_A$) other than this. Therefore, according to the conditions of a collision, it can be said that it is possible for an estimation of the velocity $v'_b$ of the ball B after a collision in the present embodiment to be executed based on vibration data without using motion data.

Further, for example, in the case where it is possible for the ball B to be regarded as static ($v_b$=0) before a collision, such as a serve in tennis, the velocity $v_b$ before a collision of the ball B is no longer an unknown quantity (at 0), in the above Formula 1 to Formula 3. In this case, Formula 1 to Formula 3 may be solved as simultaneous equations, by instead setting the velocity $v_r$ before a collision of the racket R to an unknown quantity. Also in this case, since it may not be necessary to calculate the velocity $v_r$ or $v_{rip}$ of the racket R from sensor data, and the impulse $F_t$, mass $m_r$ (or effective mass $m_{re}$), mass $m_b$, and restitution coefficient e (or apparent restitution coefficient $e_A$) other than this may be calculated, it is possible for an estimation of the velocity $v'_b$ of the ball B after a collision to be executed based on vibration data without using motion data.

(4-4 Selection of a Restitution Coefficient)

Next, a selection of a restitution coefficient will be described. A restitution coefficient is the ratio of the size of a relative velocity before and after a collision, of two colliding objects. In the above Formula 4, while the restitution coefficient between the racket R and the ball B is expressed as e, in the case where the velocity of the ball B after a collision is to be more accurately estimated, an apparent restitution coefficient $e_A$ (ACOR: Apparent Coefficient of Restitution) of the case where the racket R moves due to a collision may be used, instead of a restitution coefficient e (COR: Coefficient of Restitution) of the case were the racket R does not move due to a collision. This is because the racket R is held by a user's hand and so has room to move, at the time of an actual collision with the ball B.

It is known that the apparent restitution coefficient $e_A$ can be obtained by the following Formula 13, by using the restitution coefficient e and the mass $m_r$ of the racket R, and the effective mass $m_{re}$ of the racket R. As is obvious from Formula 13, a difference between the restitution coefficient e and the apparent restitution coefficient $e_A$ corresponds to a difference between the mass $m_r$ of the racket R and the effective mass $m_{re}$.

[Math. 10]

$$e_A = \frac{(em_{re} - m_b)}{m_{re} + m_b} \quad \text{(Formula 13)}$$

In the case where the apparent restitution coefficient $e_A$ such as described above is to be reflected in the estimation of the velocity of the ball B after a collision shown in Formula 4, the following two methods, for example, can be considered. One is a method that uses the apparent restitution coefficient $e_A$ calculated from Formula 13 as a restitution coefficient $e_{ip}$ at the collision position, for example, by using the effective mass $m_{re}$ of the racket R at the collision position calculated by the above Formula 6 or Formula 9. The other one is a method that measures the apparent restitution coefficient $e_A$ beforehand, for each position on the racket R that becomes a candidate of a collision position. In this case, it may be represented as a group of values such as an apparent restitution coefficient ACOR={$e_{A1}$, $e_{A2}$, . . . , $e_{An}$}. Note that, 1 to n are numbers given to positions on the racket R in this example. Within the above ACOR, an apparent restitution coefficient $e_A$ corresponding to a detected collision position is selected as a restitution coefficient $e_{ip}$ at the collision position.

In the above Formula 4, when the effective mass $m_{re}$ is used as the mass of the racket R, the velocity $v_{rip}$ at the collision position is used as the velocity of the racket R, and the restitution coefficient $e_{ip}$ at the collision position is used as the restitution coefficient, the velocity $v'_b$ after a collision of the ball B can be obtained by the following Formula 14.

[Math. 11]

$$v'_b = \frac{v_{rip} - \frac{F_t}{m_{re}} - e_{ip}\left(\frac{F_t}{m_b} - v_{rip}\right)}{1 + e_{ip}} \quad \text{(Formula 14)}$$

In the present embodiment, the velocity $v'_b$ of the ball after a collision can be more accurately estimated, even if the velocity $v_b$ of the ball before a collision and the velocity $v'_r$ of the racket after a collision are unknown, by estimating the effective mass $m_{re}$ of the racket R at the collision position, the velocity $v_{rip}$ of the racket R at the collision position, the restitution coefficient $e_{ip}$ at the collision position, and the impulse $F_t$. Note that, the processes may be simplified, for example, in accordance with a necessary accuracy, by using the mass $m_r$ instead of the effective mass $m_{re}$, using the velocity $v_r$ instead of the velocity $v_{rip}$ at the collision position, and using the restitution coefficient e instead of the restitution coefficient $e_{ip}$ at the collision position. That is, in the present embodiment, any one of the calculation of the effective mass $m_{re}$, the velocity $v_{rip}$, and the restitution coefficient $e_{ip}$ may be adopted as an option for improving the accuracy of estimation.

(5. Estimation of the Rotation of the Ball)

Figure 9:
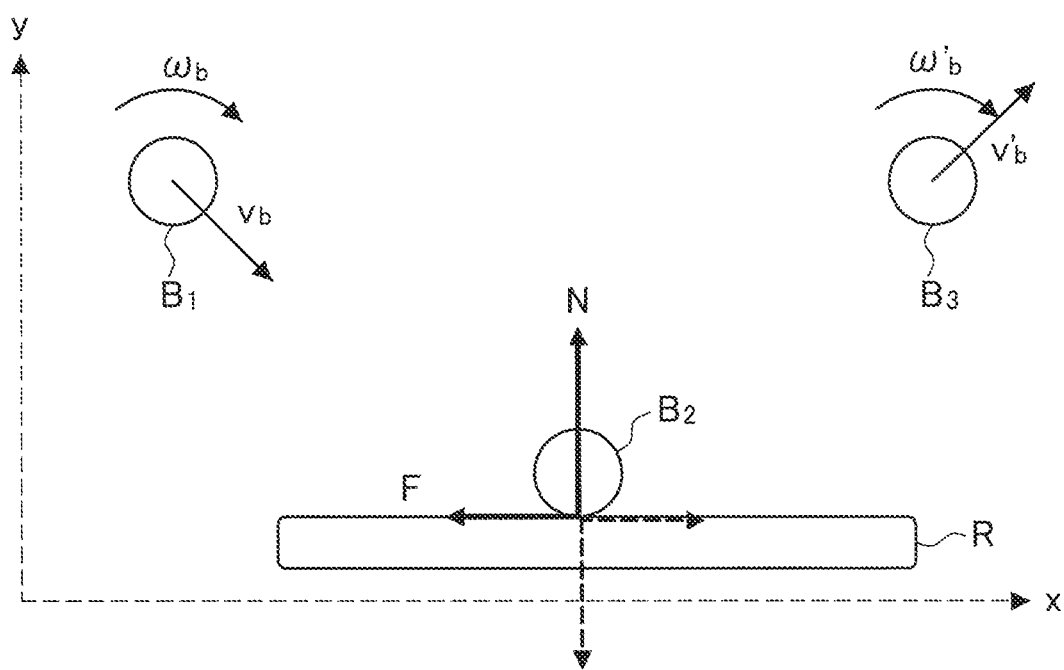
FIG. 9 is a figure for describing an estimation of the rotation of a ball after a collision in an embodiment of the present disclosure.

FIG. 9 is a figure for describing an estimation of the rotation of the ball after a collision in an embodiment of the present disclosure. With reference to FIG. 9, the racket R, the ball $B_1$ before a collision, the ball $B_2$ during a collision, and the ball $B_3$ after a collision, are shown. The radius of the ball is set to $r_b$, and the mass of the ball is set to $m_b$. The ball $B_1$ before a collision has a velocity $v_b$, and rotates with an angular velocity $\omega_b$. The ball $B_3$ after a collision has a velocity $v'_b$, and rotates with an angular velocity $\omega'_b$.

Here, when the x-axis and the y-axis are set such as illustrated, an impulse $F_x$ of the x-axis direction, received by the ball B from the racket R at the time of a collision, can be obtained by the following Formula 15. Note that, $v_{bx}$ is the x-axis direction component of the velocity $v_b$, and $v'_{bx}$ is the x-axis direction component of the velocity $v'_b$.

[Math. 12]

$$-F_x = m_b v'_{bx} - m_b v_{bx} \quad \text{(Formula 15)}$$

For example, in the estimation process of the velocity of the ball B after a collision such as described above, while the velocity $v'_b$ of the ball B after a collision is estimated, by solving Formula 1 to Formula 3, which include the three unknown quantities of $v'_r$, $v_b$ and $v'_b$, as simultaneous equations, it is possible to similarly estimate the velocity $v_b$ of the ball B before a collision. In addition, in the above process, it may also be possible to estimate the hitting angle of the ball B after a collision, based on the angle of the collision surface (head $R_H$) of the racket R at the time of a collision, and the velocity direction of the racket R at the time of a collision. If the hitting angle of the ball B is estimated, the velocities $v_b$ and $v'_b$ can be respectively divided into an x-axis direction component and a y-axis direction component, and the impulse $F_x$ can be calculated by using the above Formula 15.

Alternatively, in the case where the sensor apparatus 100 attached to the racket R includes a vibration sensor having sensitivity for the x-axis direction, the impulse $F_x$ can be obtained by the following Formula 16, similar to the case of the above Formula 5.

[Math. 13]

$$F_x = \int_1^2 f_{ip}(t) dt \quad \text{(Formula 16)}$$

When the impulse $F_x$ is obtained by the above Formula 15 or Formula 16, the following Formula 17 is derived, by a definition formula of a moment of inertia $I_b$ of the ball B (the moment of inertia $I_b$ is a constant of proportionality for an angular acceleration dω/dt of a torque $F_x r_b$ at the time of a collision).

[Math. 14]

$$F_x r_b = I_b \frac{d\omega}{dt} \quad \text{(Formula 17)}$$

In addition, in the case of a spherical shell, where the thickness within a space can be disregarded, such as the ball B being a tennis ball, the moment of inertia $I_b$ can be obtained by the following Formula 18 by using the mass $m_b$ and the radius $r_b$.

[Math. 15]

$$I_b = \frac{2}{3} m_b r_b^2 \quad \text{(Formula 18)}$$

Formula 19, which shows a relationship between the rotation angular velocities $\omega_b$ and $\omega'_b$ of the ball B before and after a collision, is derived by the above Formula 17 and Formula 18.

[Math. 16]

$$\omega'_b = \omega_b + \frac{3F_x}{2 m_b r_b} \quad \text{(Formula 19)}$$

As described above, if a value of the impulse $F_x$ can be obtained by Formula 15 or Formula 16, the rotation angular velocity $\omega'_b$ of the ball B after a collision can be obtained from the rotation angular velocity $\omega_b$ of the ball B before a collision, by substituting this for the above Formula 19. For example, in the case where it can be assumed that the ball B before a collision is static, and is hardly rotating ($\omega_b=0$) even if moving, the rotation angular velocity $\omega'_b$ of the ball B after a collision can be estimated by Formula 19. Further, in the case where the rotation angular velocity $\omega_b$ of the ball B before a collision can be estimated by some method, the rotation angular velocity $\omega'_b$ of the ball B after a collision can be estimated by Formula 19, even if not $\omega_b=0$.

Note that, in the above example, the rolling friction coefficient or slipping friction coefficient between the racket R and the ball B, the angle of the collision surface or the like have not been considered in order for simplification of the processes. While the moment of inertia $I_b$ of the ball B is calculated as a spherical shell, where the thickness within a space can be disregarded, by Formula 18, methods are well known that calculate a moment of inertia by using a spherical shell having a thickness, or a radius $r_b$ for a solid spherical body, and so Formula 18 may be replaced by arbitrarily using these methods in accordance with the shape of the ball B.

Theoretical models of an estimation of the velocity and rotation of a ball are described, for example, in R. Cross, "Effects of friction between the ball and strings in tennis", Sports Engineering, Vol. 3, Issue 2, May 2000, pp. 85-97, and Howard Brody, Rod Cross, Crawford Lindsey, "The Physics and Technology of Tennis", Racquet Tech Pub., 2002 or the like. It is possible to expand or change the process of an estimation of the velocity and rotation of a ball in the above described present embodiment, based on the theoretical models described in such literature.

For example, a track of the ball B after a collision may be estimated, as an expansion for the process of an estimation of the velocity and rotation of the ball in the present embodiment. Since it is possible to estimate the velocity (initial velocity after a collision), hitting direction, rotation axis, and rotation amount of the ball B after a collision, by processes such as described above, a track of the ball B after a collision can be estimated, by estimating a change of velocity due to gravitational acceleration, or a Magnus effect generated by rotation.

(6. Examples of Information Presentation)

EXAMPLE 1

Figure 10A:
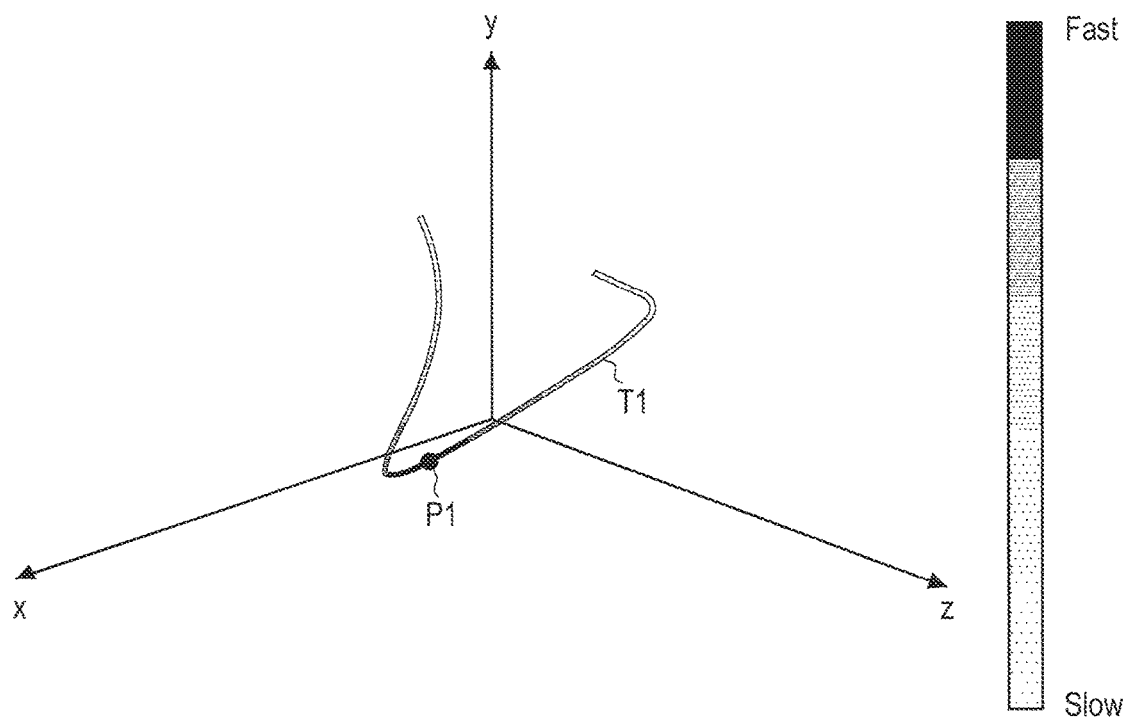
FIG. 10A is a figure that shows a first example of information presentation in an embodiment of the present disclosure.
Figure 10B:
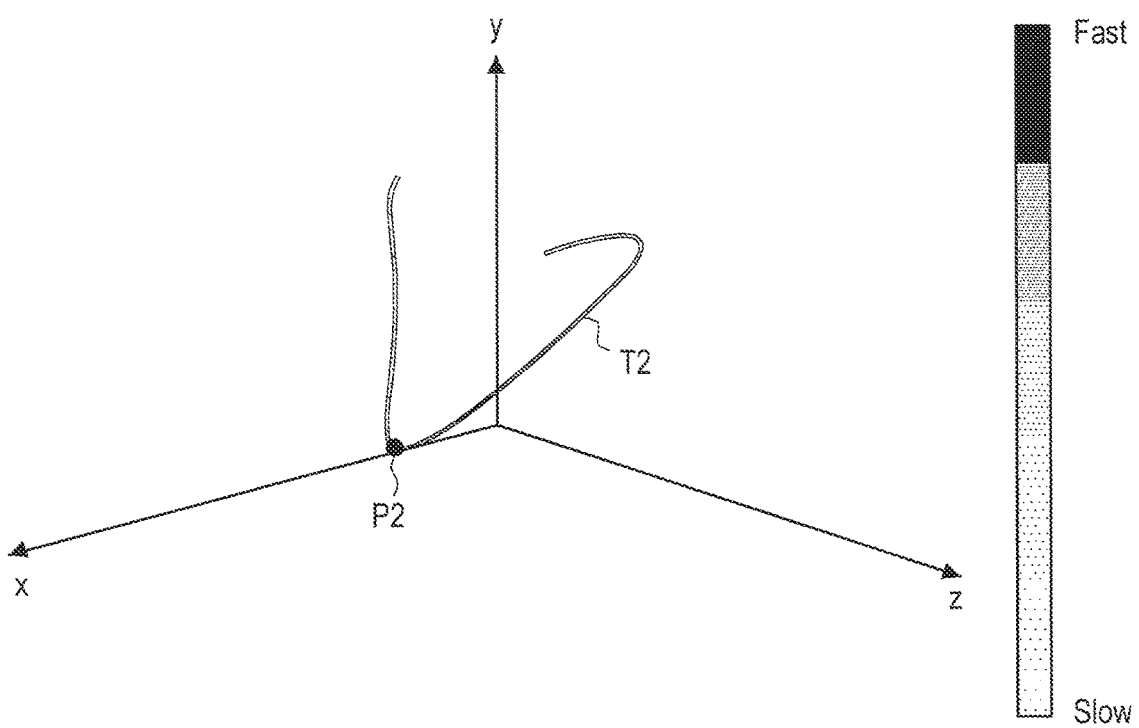
FIG. 10B is a figure that shows a first example of information presentation in an embodiment of the present disclosure.

FIG. 10A and FIG. 10B are figures that show a first example of information presentation in an embodiment of the present disclosure. In FIG. 10A and FIG. 10B, a track T of a collision position (first position) of the ball B on the racket R is displayed in a three-dimensional space (x-y-z space). The point P is the position where the racket R and the ball B collide, and the track T before and after this shows how a first position moves before and after a collision in accordance with a swing. It becomes possible for such a display to use, for example, a specific result of the collision position based on vibration data provided from the sensor apparatus 100 and a particular transfer function of the racket R, and a displacement of the collision position such as described above with reference to FIG. 8.

In addition, the track T shown in FIG. 10A and FIG. 10B is displayed with a color corresponding to the velocity of the racket R at the collision position (it is not limited to the time of a collision, and may be estimated similarly before and after this), for example, estimated by the above Formula 12. In the figure, while the track T is displayed in monochrome, the track T may be displayed in color in another example. In the example shown in FIG. 10A, the point P1 is positioned at the portion where the track T1 is displayed with the deepest color (showing a fast velocity), and it is understood that a collision of the ball B is generated in the section where the velocity of the racket R is the fastest. On the other hand, in the example shown in FIG. 10B, the point P2 is positioned shifted from the portion where the track T2 is displayed with the deepest color, and it is understood that a collision of the ball B is generated deviated from the section where the velocity of the racket R is the fastest.

EXAMPLE 2

Figure 11A:
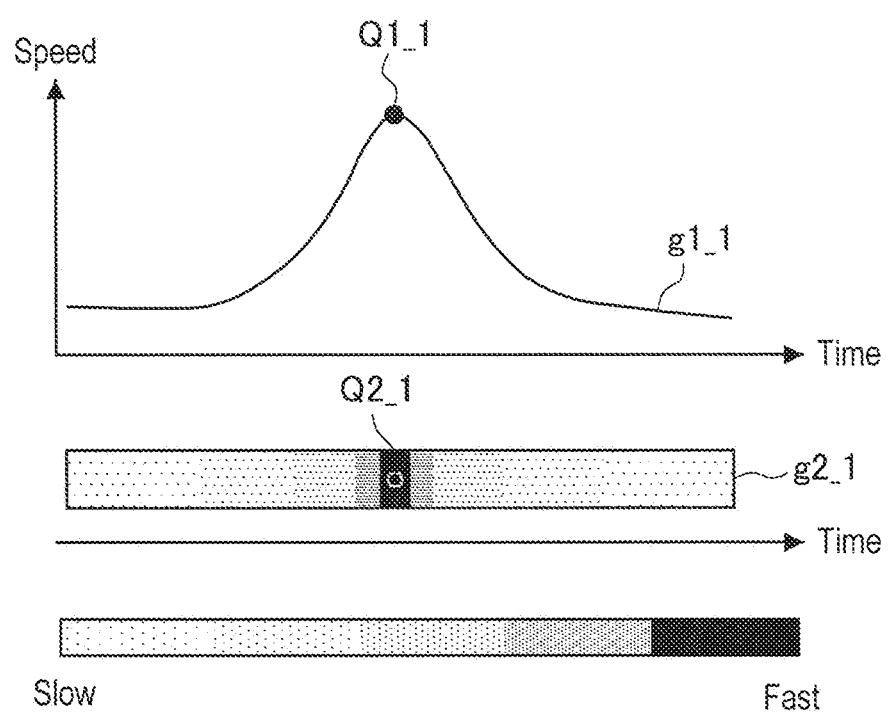
FIG. 11A is a figure that shows a second example of information presentation in an embodiment of the present disclosure.
Figure 11B:
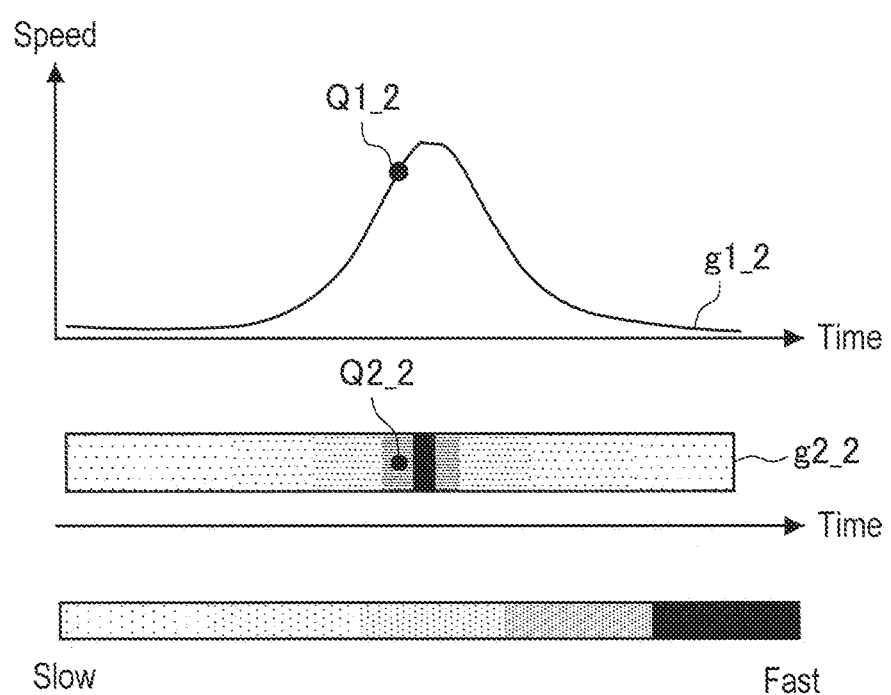
FIG. 11B is a figure that shows a second example of information presentation in an embodiment of the present disclosure.

FIG. 11A and FIG. 11B are figures that show a second example of information presentation in an embodiment of the present disclosure. In FIG. 11A and FIG. 11B, the velocity of the racket R at a collision position (first position) of the ball B is displayed by graphs g1 and g2 in a time series. Graph g1 is a line graph where the horizontal axis is set to a time axis, and the vertical axis is set to the velocity of the racket R. On the other hand, graph g2 is a graph where the velocity of the racket R is represented by a color along a time axis. In the figure, while the graphs g1 and g2 are displayed in monochrome, the graphs g1 and g2 may be displayed in color in another example. Points Q1 and Q2, which show the time when the ball B collides with the racket R, are displayed on graphs g1 and g2.

It is possible for such a display to use the velocity of the racket R at a collision position (it is not limited to the time of a collision, and may be estimated similarly before and after this), for example, estimated by the above Formula 12. In the example shown in FIG. 11A, the point Q1_1 is positioned at the top of graph g1_1, and the point Q2_1 is positioned in the section where the color is the deepest in the graph g2_1. Therefore, it is understood that a collision of the ball B is generated in the section where the velocity of the racket R is the fastest. On the other hand, in the example shown in FIG. 11B, the point Q1_2 is shifted from the top of the graph g1_2, and the point Q2_2 is deviated from the section where the color is the deepest in the graph g2_2. Therefore, it is understood that a collision of the ball B is generated deviated from the section where the velocity of the racket R is the fastest.

By information presentations such as described above, for example, a user can intuitively comprehend whether or not the ball B is hit in the section where the velocity of the racket R is the fastest.

(7. Hardware Configurations)

Next, examples of hardware configurations for implementing the sensor apparatus and the analysis apparatus (in the above described examples, the smart phone or the server) according to an embodiment of the present disclosure will be described with reference to FIG. 12 and FIG. 13.

(Sensor Apparatus)

Figure 12:
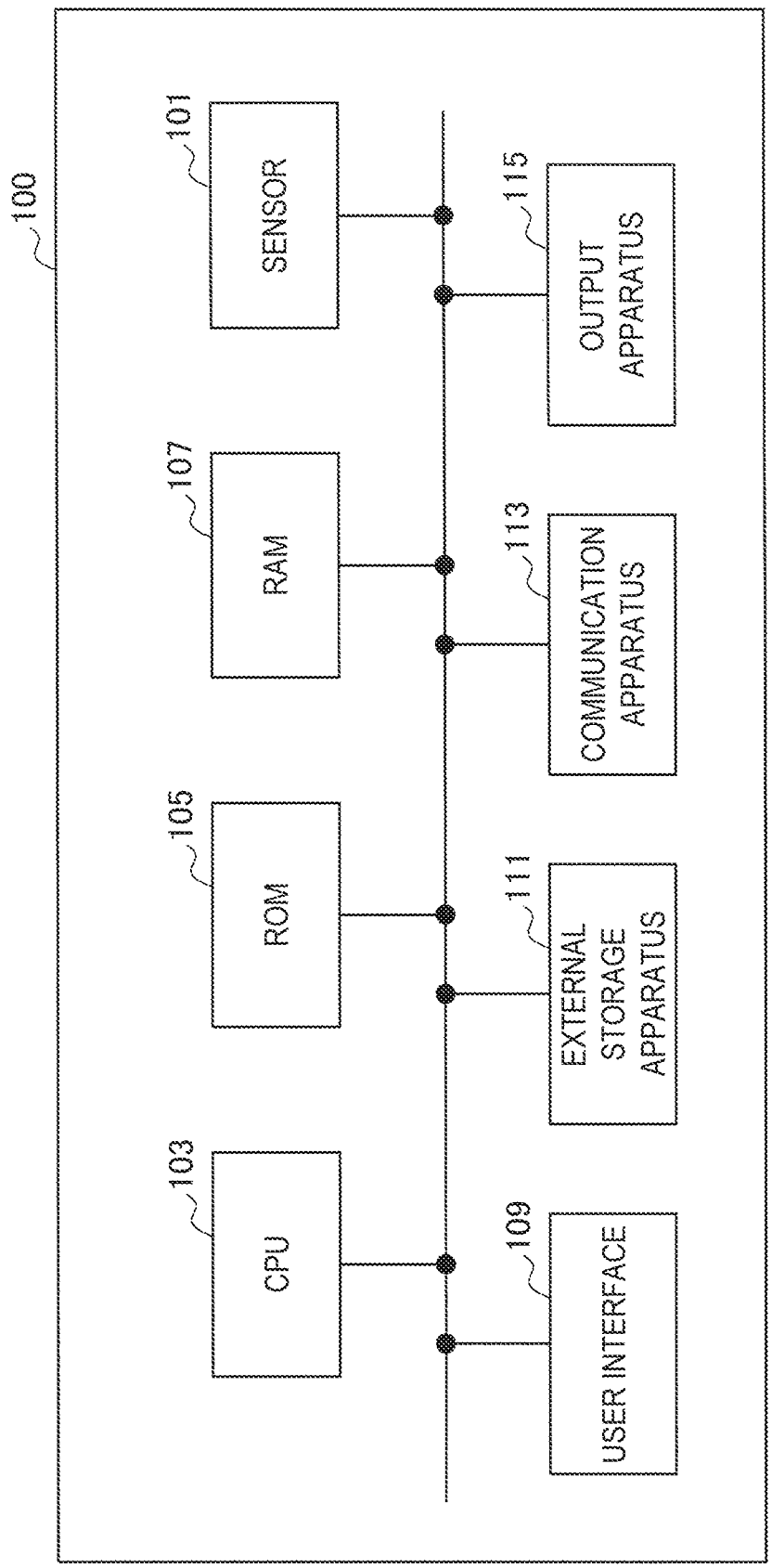
FIG. 12 is a figure that shows an example of a hardware configuration of a sensor apparatus according to an embodiment of the present disclosure.

FIG. 12 is a figure that shows an example of a hardware configuration of the sensor apparatus according to an embodiment of the present disclosure. With reference to FIG. 12, the sensor apparatus 100 may include a sensor 101, a Central Processing Unit (CPU) 103, a Read Only Memory (ROM) 105, a Random Access Memory (RAM) 107, a user interface 109, an external storage apparatus 111, a communication apparatus 113, and an output apparatus 115. These elements are mutually connected by a bus, for example.

For example, the sensor 101 includes an acceleration sensor, an angular velocity sensor, a vibration sensor, a temperature sensor, a pressure sensor (including a press switch), a Global Positioning System (GPS) receiver or the like, and implements the input unit 410 in the above described functional configuration. The sensor 101 may include a camera (imaging sensor) or a microphone (audio sensor).

The CPU 103, the ROM 105 and the RAM 107 implement various types of functions with software, by reading and executing program instructions, for example, recorded in the external storage apparatus 111. In the embodiments of the present disclosure, functions such as control of the entire sensor apparatus 100 may be implemented, for example, by the CPU 103, the ROM 105 and the RAM 107. Further, a part or all of the functions of the processing unit 420 may be implemented in the above function configuration, by the CPU 103, the ROM 105, and the RAM 107 of the sensor apparatus 100.

The user interface 109 is, for example, an input apparatus such as buttons or a touch panel, which receives user operations of the sensor apparatus 100. For example, operations of a user may instruct the start or completion of the transmission of sensor information from the sensor apparatus.

The external storage apparatus 111 stores various types of information related to the sensor apparatus 100. For example, program instructions for causing functions to be implemented by software in the CPU 103, the ROM 105 and RAM 107 may be stored in the external storage apparatus 111, or data acquired by the sensor 101 may be cached temporarily. When considering that the sensor apparatus 100 is mounted in a hitting tool or the like, it is desirable to use a sensor apparatus, for example, with a strong impact such as a semiconductor memory, as the external storage apparatus 111.

The communication apparatus 113 communicates with the analysis apparatus 600, which will be described later, by various types of wired or wireless communication systems. Further, the communication apparatus 113 may directly communicate with the analysis apparatus 600 by inter-device communication, or may communicate with the analysis apparatus 600 via a network such as the internet.

The output apparatus 115 is constituted by an apparatus capable of outputting information as light, audio or images. For example, the output apparatus 115 may output information that notifies a detection of a time or play event in the sensor apparatus 100, or may output a visual or aural notification to a user, based on an analysis result received from the analysis apparatus 600 or an analysis result calculated in the sensor apparatus 100. For example, the output apparatus 115 includes, for example, a display such as a lamp of an LED or the like or an LCD, a speaker, a vibrator or the like.

(Analysis Apparatus)

Figure 13:
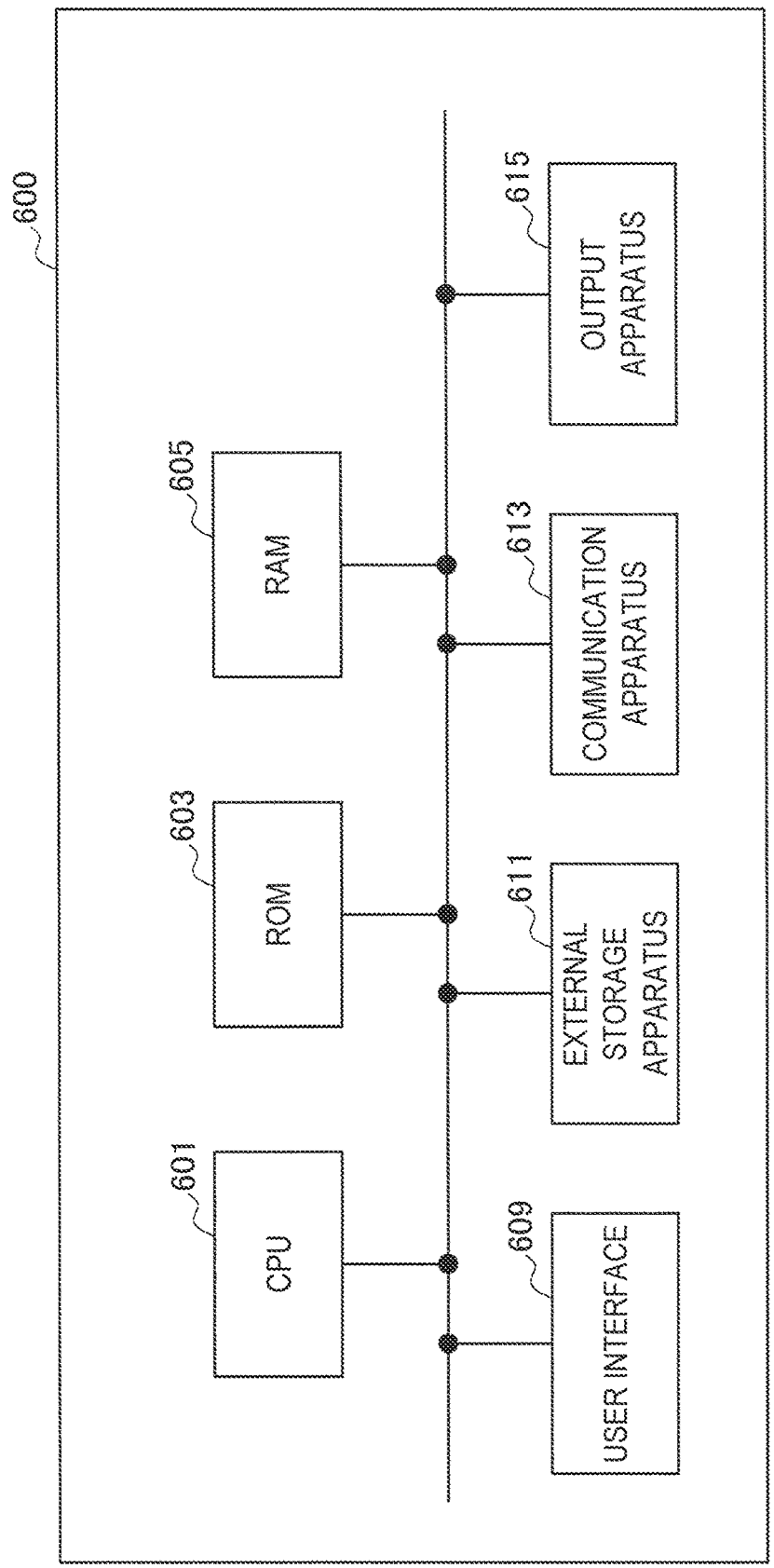
FIG. 13 is a figure that shows an example of a hardware configuration of an analysis apparatus according to an embodiment of the present disclosure.

FIG. 13 is a figure that shows an example of a hardware configuration of the analysis apparatus according to an embodiment of the present disclosure. The analysis apparatus 600 may implement, for example, the analysis apparatus according to an embodiment of the present disclosure, or the smart phone 200 or the server 300 described above. Note that, as described above, the analysis apparatus may be implemented by the sensor apparatus 100.

The analysis apparatus 600 may include a CPU 601, a ROM 603, a RAM 605, a user interface 609, an external storage apparatus 611, a communication apparatus 613, and an output apparatus 615. These elements are mutually connected by a bus, for example.

The CPU 601, the ROM 603 and the RAM 605 implement various types of functions with software, by reading and executing program instructions, for example, recorded in the external storage apparatus 611. In the embodiments of the present disclosure, control of the entire analysis apparatus 600, functions of the processing unit 420 in the above described functional configuration or the like, may be implemented, for example, by the CPU 601, the ROM 603 and the RAM 605.

The user interface 609 is, for example, an input apparatus such as buttons or a touch panel, which receives user operations of the analysis apparatus 600.

The external storage apparatus 611 stores various types of information related to the analysis apparatus 600. For example, program instructions for causing functions to be implemented by software in the CPU 601, the ROM 603 and RAM 605 may be stored in the external storage apparatus 611, or sensor information received by the communication apparatus 613 may be cached temporarily. Further, a log of analysis results may be accumulated in the external storage apparatus 611.

The output apparatus 615 is constituted by an apparatus capable of visually or aurally notifying information to a user. For example, the output apparatus 615 may be a display device such as a Liquid Crystal Display (LCD), or an audio output device such as a speaker or headphones. The output apparatus 615 outputs a result obtained by the processes of the analysis apparatus 600 as video images such as text or pictures, or outputs the results as audio such as voices or sounds. For example, information such as that described with reference to FIGS. 11A, 11B, 12A, and 12B may be output towards a user via a display device such as an LCD.

Heretofore, examples of the hardware configurations of the sensor apparatus 100 and the analysis apparatus 600 have been shown. Each of the above described constituent elements may be constituted by using generic members, or may be constituted by hardware specialized for the functions of each of the constituent elements. Such a configuration may be appropriately changed in accordance with the technology level at the time of implementation.

8. CONCLUSION

For example, the embodiments of the present disclosure may include an analysis apparatus such as that described above (an information processing terminal such as a smart phone, a server, or a sensor apparatus), a system, an information processing method executed by the analysis apparatus or the system, a program for causing the analysis apparatus to function, and a non-temporarily tangible medium on which programs are recorded.

It should be understood by those skilled in the art that various modifications, combinations, sub-combinations and alterations may occur depending on design requirements and other factors insofar as they are within the scope of the appended claims or the equivalents thereof.

Further, the effect described in the present disclosure is not limited to that specified or illustrated. That is, the technology according to the present disclosure may accomplish other effects obvious to a person skilled in the art from the description of the present disclosure, along with the above described effect or instead of the above described effect.

Additionally, the present technology may also be configured as below.

(1) An analysis apparatus, including:
an acquisition unit configured to acquire vibration data showing a vibration generated in a first object by having a second object come into contact with a first position on the first object;
a first analysis processing unit configured to specify the first position by comparing a vibration characteristic shown by the vibration data, and a vibration characteristic defined for each position where the second object may come into contact with the first object; and
a second analysis processing unit configured to estimate a velocity after the contact of the second object based on a velocity of the first object and the first position.

(2) The analysis apparatus according to (1),
wherein the second analysis processing unit estimates the velocity after the contact of the second object based on an effective mass of the first object at the first position.

(3) The analysis apparatus according to (1) or (2),
wherein the second analysis processing unit calculates an impulse given to the second object by the first object based on the vibration characteristic defined for the first position and the vibration data, and estimates the velocity after the contact of the second object based on the impulse.

(4) The analysis apparatus according to (3),
wherein the second analysis processing unit calculates the impulse from the vibration data by an inverse operation using a transfer function included in the vibration characteristic defined for the first position.

(5) The analysis apparatus according to any one of (1) to (4),
wherein the acquisition unit additionally acquires motion data showing a displacement and rotation of the first object in a section including the contact, and
wherein the second analysis processing unit estimates the velocity after the contact of the second object based on a posture of the first object estimated based on the motion data.

(6) The analysis apparatus according to (5),
wherein the second analysis processing unit estimates the velocity after the contact of the second object based on a velocity direction at a time of the contact of the first object estimated based on the posture.

(7) The analysis apparatus according to (5) or (6),
wherein the second analysis processing unit estimates a rotation amount after the contact of the second object based on a velocity direction at a time of the contact of the first object estimated based on the posture.

(8) The analysis apparatus according to any one of (1) to (7),
wherein the second analysis processing unit selects or calculates a restitution coefficient at the contact in accordance with the first position.

(9) The analysis apparatus according to (8),
wherein the second analysis processing unit calculates the restitution coefficient based on an effective mass of the first object at the first position.

(10) The analysis apparatus according to any one of (1) to (8), further including:
a third analysis processing unit configured to estimate a track after the contact of the second object based on the velocity after the contact of the second object.

(11) An analysis method, including:
acquiring vibration data showing a vibration generated in a first object by having a second object come into contact with a first position on the first object;
specifying the first position by comparing a vibration characteristic shown by the vibration data, and a vibration characteristic defined for each position where the second object may come into contact with the first object; and
estimating a velocity after the contact of the second object based on a velocity of the first object and the first position.

(12) A recording medium having a program stored therein, the program causing a computer to implement:
a function of acquiring vibration data showing a vibration generated in a first object by having a second object come into contact with a first position on the first object;
a function of specifying the first position by comparing a vibration characteristic shown by the vibration data, and a vibration characteristic defined for each position where the second object may come into contact with the first object; and
a function of estimating a velocity after the contact of the second object based on a velocity of the first object and the first position.

REFERENCE SIGNS LIST

10, 40 system
100 sensor apparatus
200 smart phone 300 server
410 input unit
411 vibration sensor
413 motion sensor
415 another sensor
420 processing unit
421 collision detection unit
423 physical calculation unit
4231 collision analysis unit
4233 hitting ball estimation unit
44235 hitting ball track estimation unit
425 output correction unit
430 output unit
431 display
433 speaker
435 another output unit

The invention claimed is:

1. An analysis apparatus, comprising:
at least one sensor configured to acquire vibration data that represents vibration generated in a first object; and
at least one processor configured to:
extract a portion of the acquired vibration data of a section region based on a contact of a second object at a first position on the first object,
wherein the section region includes the first position;
determine the first position, on the first object, of the contact of the second object, based on a comparison of the extracted portion of the acquired vibration data and a vibration characteristic of a plurality of vibration characteristics,
wherein the plurality of vibration characteristics are defined for each of a plurality of positions on the first object;
calculate a first velocity of the first object, based on an angular velocity of the at least one sensor and a displacement of the first position from a second position of the at least one sensor;
estimate a second velocity after the contact of the second object with the first object, based on the calculated first velocity of the first object and an effective mass of the first object at the first position;
estimate, based on the estimated second velocity, trajectory information for motion of the second object after the contact with the first object; and
control a display screen to display the estimated trajectory information.

2. The analysis apparatus according to claim 1,
wherein the at least one processor is further configured to:
calculate an impulse corresponding to the contact of the second object with the first object, based on the vibration characteristic and the extracted portion of the acquired vibration data; and
estimate the second velocity after the contact of the second object with the first object, based on the calculated impulse.

3. The analysis apparatus according to claim 2,
wherein the at least one processor is further configured to calculate the impulse from the extracted portion of the acquired vibration data, based on a transfer function included in the vibration characteristic.

4. The analysis apparatus according to claim 1, wherein
the at least one sensor includes a motion sensor configured to acquire motion data indicating a rotation of the first object in the section region of the first object, and
the at least one processor is further configured to:
estimate a posture of the first object based on the motion data, and
estimate the second velocity after the contact of the second object, based on the estimated posture of the first object.

5. The analysis apparatus according to claim 4,
wherein the at least one processor is further configured to:
estimate, based on the estimated posture, a velocity direction of the first object at a time of the contact of the second object with the first object; and
estimate the second velocity after the contact of the second object, based on the estimated velocity direction at the time of the contact of the second object with the first object.

6. The analysis apparatus according to claim 4,
wherein the at least one processor is further configured to:
estimate, based on the estimated posture, a velocity direction of the first object at a time of the contact of the second object with the first object; and
estimate a rotation amount of the second object after the contact of the second object, based on the estimated velocity direction at the time of the contact of the second object with the first object.

7. The analysis apparatus according to claim 1,
wherein the at least one processor is further configured to one of select a restitution coefficient for the contact of the second object with the first object or calculate the restitution coefficient for the contact of the second object with the first object, based on the first position.

8. The analysis apparatus according to claim 7,
wherein the at least one processor is further configured to calculate the restitution coefficient based on the effective mass of the first object at the first position.

9. An analysis method, comprising:
in an analysis apparatus:
acquiring, from at least one sensor, vibration data that represents vibration generated in a first object;
extracting a portion of the acquired vibration data of a section region based on a contact of a second object at a first position on the first object,
wherein the section region includes the first position;
determining the first position, on the first object, of the contact of the second object, based on a comparison of the extracted portion of the acquired vibration data and a vibration characteristic of a plurality of vibration characteristics,
wherein the plurality of vibration characteristics are defined for each of a plurality of positions on the first object;
calculating a first velocity of the first object, based on an angular velocity of the at least one sensor and a displacement of the first position from a second position of the at least one sensor;
estimating a second velocity after the contact of the second object with the first object, based on the calculated first velocity of the first object and an effective mass of the first object at the first position;
estimating, based on the estimated second velocity, trajectory information for motion of the second object after the contact with the first object; and
controlling a display screen to display the estimated trajectory information.

10. A non-transitory computer-readable medium having stored thereon, computer-executable instructions which, when executed by a computer, cause the computer to execute operations, the operations comprising:
acquiring, from at least one sensor, vibration data that represents vibration generated in a first object;

extracting a portion of the acquired vibration data of a section region based on a contact of a second object at a first position on the first object, wherein the section region includes the first position;

determining the first position, on the first object, of the contact of the second object, based on a comparison of the extracted portion of the acquired vibration data and a vibration characteristic of a plurality of vibration characteristics,
   wherein the plurality of vibration characteristics are defined for each of a plurality of positions on the first object;

calculating a first velocity of the first object, based on an angular velocity of the at least one sensor and a displacement of the first position from a second position of the at least one sensor;

estimating a second velocity after the contact of the second object with the first object, based on the calculated first velocity of the first object and an effective mass of the first object at the first position;

estimating, based on the estimated second velocity, trajectory information for motion of the second object after the contact with the first object; and controlling a display screen to display the estimated trajectory information.

11. An analysis apparatus, comprising:

a sensor apparatus that includes:
   a first sensor configured to acquire vibration data, based on a contact of a second object at a first position on a first object, wherein the vibration data represents vibration generated in the first object; and
   a second sensor configured to acquire motion data indicating a rotation of the first object in the first position; and at least one processor configured to:
   determine the first position, on the first object, of the contact of the second object, based on a comparison of the acquired vibration data and a vibration characteristic of a plurality of vibration characteristics,
      wherein the plurality of vibration characteristics are defined for each of a plurality of positions on the first object;
   estimate a posture of the first object based on the acquired motion data;
   calculate a first velocity of the first object, based on an angular velocity of the sensor apparatus, a displacement of the first position from a second position of the sensor apparatus, and the estimated posture of the first object;
   estimate a second velocity after the contact of the second object with the first object, based on the calculated first velocity of the first object and an effective mass of the first object at the first position;
   estimate, based on the estimated second velocity, a trajectory for motion of the second object after the contact with the first object; and
   control a display screen to display the estimated trajectory.

* * * * *